US011148999B2

(12) United States Patent
Riesinger et al.

(10) Patent No.: US 11,148,999 B2
(45) Date of Patent: Oct. 19, 2021

(54) NITRIC OXIDE DONORS

(71) Applicant: MedChem Partners, LLC, Lexington, MA (US)

(72) Inventors: Steven Riesinger, Lexington, MA (US); Tsvetelina Lazarova, Lexington, MA (US); Zinadia Ribkovskaia, Lexington, MA (US)

(73) Assignee: MedChem Partners, LLC, Lexington, MA (US)

( * ) Notice: Subject to any disclaimer, the term of this patent is extended or adjusted under 35 U.S.C. 154(b) by 40 days.

(21) Appl. No.: 16/308,941

(22) PCT Filed: Jun. 21, 2017

(86) PCT No.: PCT/US2017/038509
§ 371 (c)(1),
(2) Date: Dec. 11, 2018

(87) PCT Pub. No.: WO2017/223182
PCT Pub. Date: Dec. 28, 2017

(65) Prior Publication Data

US 2019/0345099 A1 Nov. 14, 2019

Related U.S. Application Data

(60) Provisional application No. 62/353,166, filed on Jun. 22, 2016.

(51) Int. Cl.

| | |
|---|---|
| ***A61K 31/197*** | (2006.01) |
| ***A61K 31/23*** | (2006.01) |
| ***A61K 31/231*** | (2006.01) |
| ***A61K 31/336*** | (2006.01) |
| ***A61K 31/40*** | (2006.01) |
| ***A61K 31/4035*** | (2006.01) |
| ***A61K 31/661*** | (2006.01) |
| ***A61K 9/06*** | (2006.01) |
| ***A61P 17/02*** | (2006.01) |
| ***C07C 245/24*** | (2006.01) |
| ***C07D 207/50*** | (2006.01) |
| ***C07D 403/12*** | (2006.01) |

(52) U.S. Cl.
CPC .............. *C07C 245/24* (2013.01); *A61K 9/06* (2013.01); *A61K 31/197* (2013.01); *A61P 17/02* (2018.01); *C07D 207/50* (2013.01); *C07D 403/12* (2013.01); *A61K 31/23* (2013.01); *A61K 31/231* (2013.01); *A61K 31/336* (2013.01); *A61K 31/40* (2013.01); *A61K 31/4035* (2013.01); *A61K 31/661* (2013.01)

(58) Field of Classification Search
CPC .... C07C 245/24; C07D 207/50; C07D 403/12
See application file for complete search history.

(56) References Cited

U.S. PATENT DOCUMENTS

| | | | |
|---|---|---|---|
| 4,900,478 A | 2/1990 | Gross | |
| 8,597,720 B2 | 12/2013 | Hoffmann et al. | |
| 2009/0186859 A1 | 7/2009 | Velazquez et al. | |
| 2016/0106765 A1 | 4/2016 | Cardinal-David et al. | |

FOREIGN PATENT DOCUMENTS

| | | | |
|---|---|---|---|
| WO | WO-9509612 A1 * | 4/1995 | ............. A61K 31/13 |
| WO | WO-2009004164 A2 * | 1/2009 | ................ A61P 9/12 |
| WO | WO-2014012074 A2 * | 1/2014 | ........... C07D 403/14 |

OTHER PUBLICATIONS

Cordi et al. WO 2009004164 A2 (pub. Jan. 8, 2009), partial English machine translation (specification). (Year: 2009).*
Bensel et al. Chem. Eur. J. 2001,7, 4604-4612. (Year: 2001).*
Baysal, "Nitric Oxide II: Therapeutic Uses and Clinical Applications," Turk J Med Sci., No. 32, pp. 1-6, 2002.
Carpenter, et al., "Nitric oxide release: Part II. Therapeutic applications," Chem. Soc. Rev., No. 41, pp. 3742-3752, 2012.
Cavet, et al., "Nitric Oxide (NO): AN Emerging Target for the Treatment of Glaucoma," IOVS, vol. 55, No. 8, pp. 5005-5015, Aug. 2014.
Coulter, et al. "Nitric oxide: A novel therapeutic for cancer," Nitric Oxide19, pp. 192-198, 2008.
Nageswararao, et al., "Nitric Oxide: A Novel Therapeutic Target," IJPSR, vol. 2, No. 7, pp. 1603-1615, 2011.
Namkoong, et al., "Therapeutic Application of Nitric Oxide in Human Diseases," Biomolecules & Therapeutics, vol. 18, No. 4, pp. 351-362, 2010.
Vidal, et al., "Nitric oxide synthase in retina and optic nerve head of rat with increased intraocular pressure and effect of timolo," Brain Research Bulletin, vol. 70, pp. 406-413, 2006.

* cited by examiner

*Primary Examiner* — Amanda L. Aguirre
(74) *Attorney, Agent, or Firm* — Morgan, Lewis & Bockius LLP

(57) ABSTRACT

The present invention provides, in part a novel class of nonoate compounds which exhibit nitric oxide releasing activity and their pharmaceutically acceptable salts, esters and prodrugs. The compounds release nitric oxide upon activation by contact with plasma. The present invention also relates to the use of the disclosed compounds to deliver nitric oxide to treat disorders arising from nitric oxide dysregulation.

18 Claims, 5 Drawing Sheets

A.

B.

A.

B.

A.

B.

C.

D.

NITRIC OXIDE DONORS

PRIORITY

This application relates, in part, to novel NONOate compounds which are useful in the treatment of various disorders including disorders arising from nitric oxide dysregulation. More particularly, the present invention relates to a novel class of NONOate compounds, compositions containing such compounds and methods for using the same.

FIELD

This application relates, in part, to novel nonoate compounds which are useful in the treatment of various disorders including disorders arising from nitric oxide dysregulation. More particularly, the present invention relates to a novel class of nonoate compounds, compositions containing such compounds and methods for using the same.

BACKGROUND

Nitric oxide (NO) is a gaseous compound which is known to be involved in a number of biological functions including its role in the erectile response. In addition to its function in overcoming erectile dysfunction NO function has been known to function in numerous medical areas such as vasodilation, cardiovascular health, endothelial health, and wound healing.

Therefore, exogenous NO is a potential therapeutic agent in a variety of diseases. NO can be administered in gaseous form (e.g. respiratory route) in specific cases, but this compound is known to react with a wide number of molecules and also can be oxidized in solution to $NO_2$ by $O_2$. In addition, NO only lasts about 10 ms to 1 sec in biological media. Furthermore local lack or excess of NO can be deleterious for biological systems. Therefore, strategies to produce stable NO carriers, such as NO-releasing compounds, have been developed Regardless, commercially available NO-releasing compounds remain sparse. The only direct NO releasing drug clinically available in the United States is sodium nitroprusside, but five cyanide ions are released for every NO molecule, limiting its use because of cyanide toxicity.

Accordingly, improved and more efficient nitric oxide releasing compounds are needed in the art.

SUMMARY

The present invention provides a novel class of NONOate compounds which exhibit antibacterial activity and their pharmaceutically acceptable salts, esters and prodrugs thereof.

In one embodiment the present invention provides compounds represented by Formula I (I)

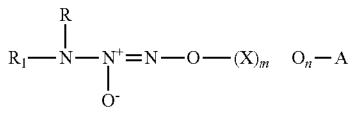

or a pharmaceutically acceptable salt, ester or prodrug thereof, where X is $CH_2$ or $CHCH_3$, m is 0, 1, 2 or 3 and n is 0 or 1, provided that when m is 0 n is 0;

R is alkyl, preferably having from 1 to 6 carbon atoms;

$R_1$ is alkyl, preferably having from 1 to 6 carbon atoms; or R and $R_1$ taken together are carbon atoms to form a 5-7 member heterocyclic ring, said 5-7 member heterocyclic ring being optionally substituted with $—CH_2OH$;

A is a negative charge with a $Na^+$ counterion, $—B(OR_2)(OR_3)$, $—(Y)_p—C(═O)—R_4$,

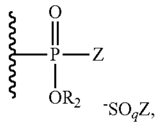

$^-SO_qZ$, 1,3-dioxoisoindolin-2-yl, heterocycloalkyl, or a lipid, where

Y is $—CH_2—$ and p is 0 or 1;

q is 0, 1 or 2;

$R_2$ and $R_3$ are the same or different and are alkyl, preferably having from 1 to 6 carbon atoms or aryl, optionally substituted with —OH;

$R_4$ is alkyl (optionally substituted with $—NH_2$), alkenyl, heteroalkyl (optionally substituted with one or more moieties independently selected from oxo, halo,

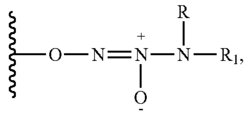

aryl, N-alkyl, N-aryl, O-alkyl or O-aryl; and

Z is alkyl, aryl, N-alkyl, N-aryl, O-alkyl or O-aryl.

In various embodiments, the compound of Formula I is selected from compounds (1)-(33) as described herein.

In various embodiments, the compound of the invention is selected from (34)-(37) as described herein.

In various embodiments, the compounds of the invention are stable in storage. In various embodiments, the compounds release nitric oxide upon activation by plasma.

In various embodiments, the compounds of the invention are capable of releasing nitric oxide under physiological conditions. In various embodiments, the compounds of the invention release nitric oxide upon activation by contact with plasma. In various embodiments, the compounds of the invention generate a prolonged flux of NO at the desired area of interest.

Another embodiment of the invention pertains to pharmaceutical compositions comprising a therapeutically effective amount of compound(s) of the present invention in combination with a pharmaceutically acceptable carrier. The compositions are useful in the modification of pathways which are regulated by nitric oxide. The compositions are useful in the treatment of various disorders including wound healing, cardiovascular dysfunction, circulatory dysfunction, infections (e.g. bacterial, fungal, viral, etc.), ophthalmic dysfunctions, reperfusion, thrombosis or other disorders of nitric oxide dysregulation. The compositions are also useful in drug delivery when co-administered with a therapeutically useful amount of a drug to increase the permeability of the drug thus increasing penetration of the drug into the target tissue.

In another embodiment of the invention there is provided a method of delivering a therapeutically useful amount of nitric oxide in a therapeutically useful manner by cleaving a capping group. Cleavage of the capping group is facilitated by exposure to a biological environment such as blood, plasma, wound surfaces or contact with bodily fluids. Cleavage of the capping group is effected by the enzymatic or hydrolytic activity of the biological environment. By manipulation of the compound the kinetics of nitric oxide release can be controlled to be useful in a number of indications.

For example, a compound of the invention may be capped with an ester group which is cleaved by esterases in the blood or a wound bed. The capping group may be selected such that the kinetics of its cleavage reaction are adjustable. For example, where the capping group is an ester, a primary ester, e.g., a methyl ester, will be cleaved much more readily and typically will have a shorter half-life than a tertiary ester, e.g., t-butyl ester, which typically will have a much longer half-life. Adjusting the kinetics of cleavage of the compound and consequently the release kinetics will be advantageous to tailor nitric oxide release for specific indications.

DETAILED DESCRIPTION

Figure 1:
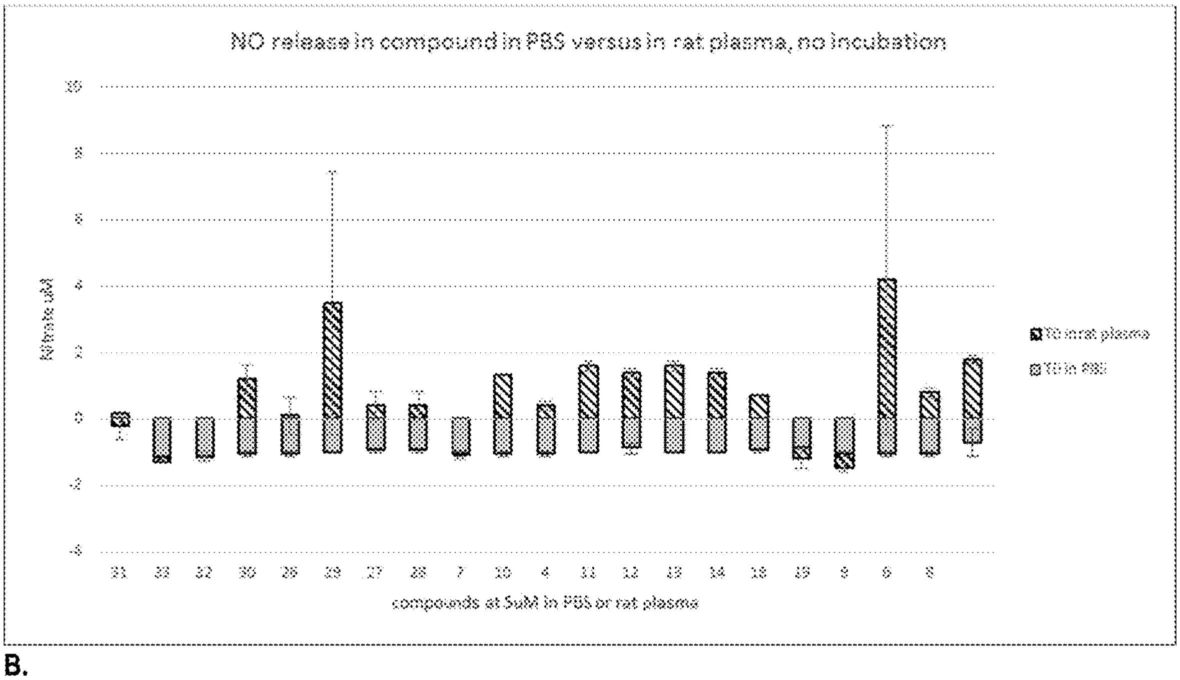
FIG. 1, panel A, shows NO release by various disclosed compounds (X axis) at 5 μM in PBS as compared to rat plasma. In these experiments, there was no incubation time. Panel B shows NO release as in panel A but with three hours of incubation at 37° C.
Figure 1:
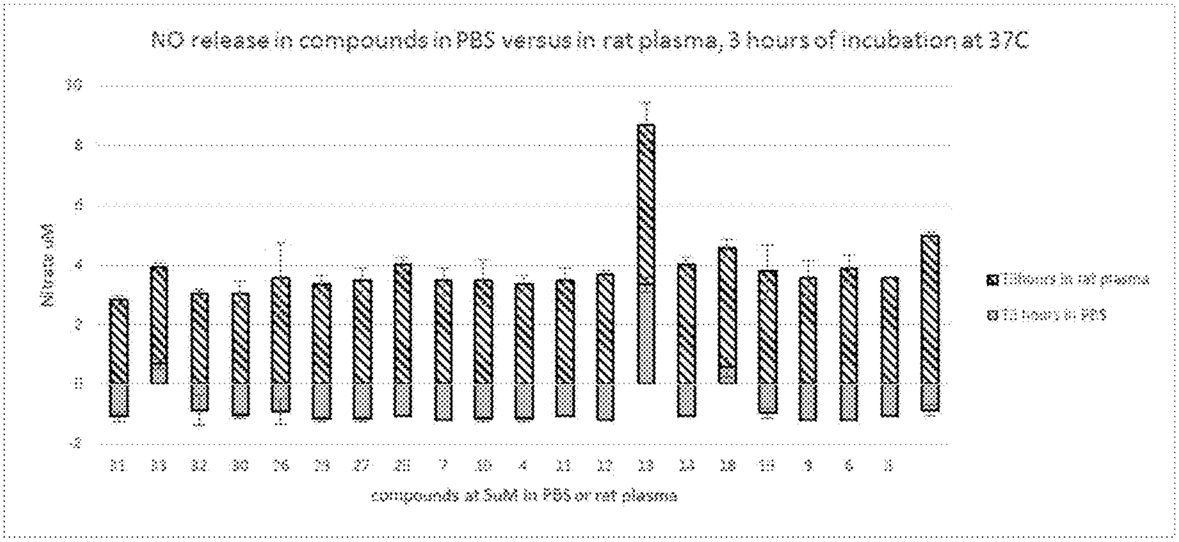

The present invention is based, in part, on the discovery of improved NO-releasing compounds as described herein.

In one aspect, the invention relates to a compound represented by Formula I:

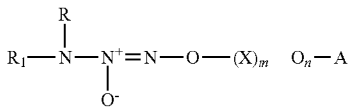

(I)

where the variables are described above.

In some embodiments, the compound of Formula I is:

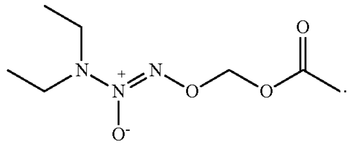

(1)

In some embodiments, the compound of Formula I is:

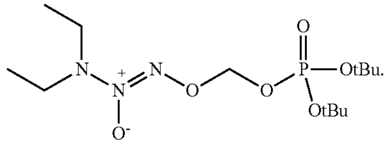

(2)

In some embodiments, the compound of Formula I is:

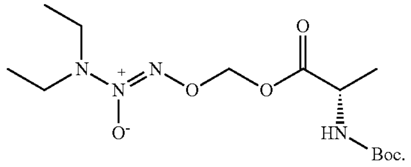

(3)

In some embodiments, the compound of Formula I is:

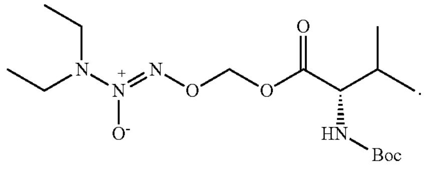

(4)

In some embodiments, the compound of Formula I is:

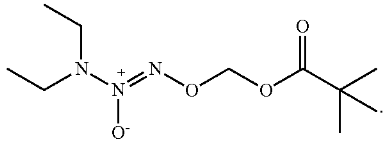

(5)

In some embodiments, the compound of Formula I is:

(6)

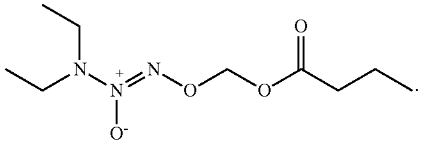

In some embodiments, the compound of Formula I is:

(7)

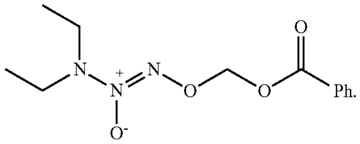

In some embodiments, the compound of Formula I is:

(8)

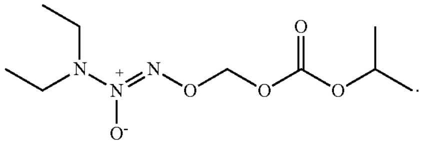

In some embodiments, the compound of Formula I is:

(9)

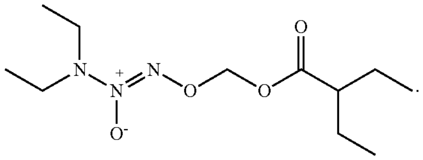

In some embodiments, the compound of Formula I is:

(10)

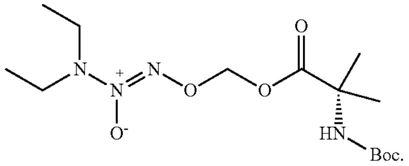

In some embodiments, the compound of Formula I is:

(11)

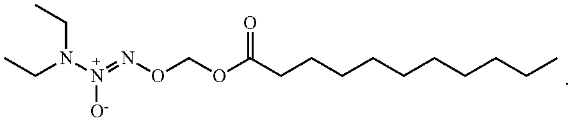

In some embodiments, the compound of Formula I is:

(12)

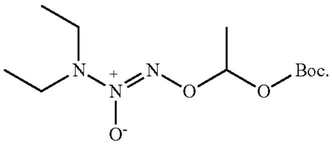

In some embodiments, the compound of Formula I is:

(13)

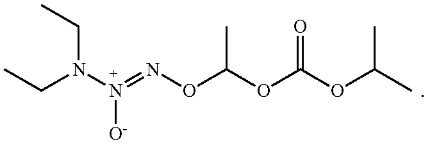

In some embodiments, the compound of Formula I is:

(14)

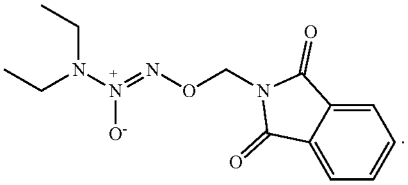

In some embodiments, the compound of Formula I is:

(15)

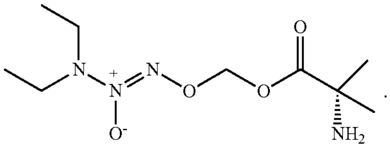

In some embodiments, the compound of Formula I is:

(16)

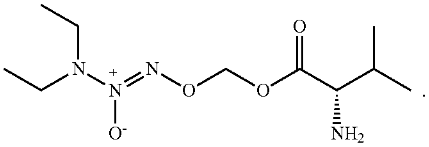

In some embodiments, the compound of Formula I is:

(17)

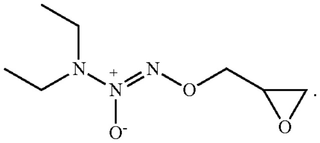

In some embodiments, the compound of Formula I is:

(18)

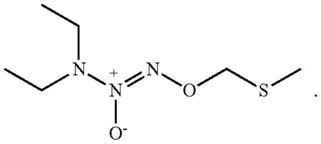

In some embodiments, the compound of Formula I is:

(23)

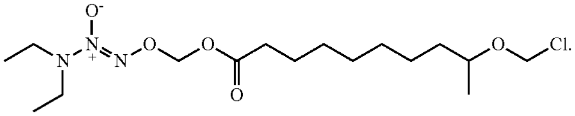

In some embodiments, the compound of Formula I is:

(24)

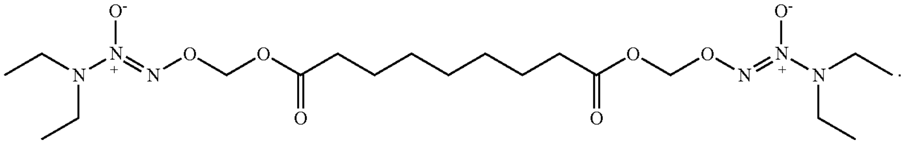

In some embodiments, the compound of Formula I is:

(19)

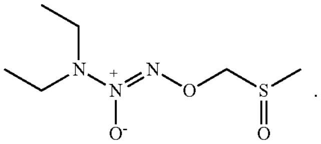

In some embodiments, the compound of Formula I is:

(20)

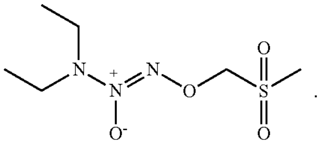

In some embodiments, the compound of Formula I is:

(21)

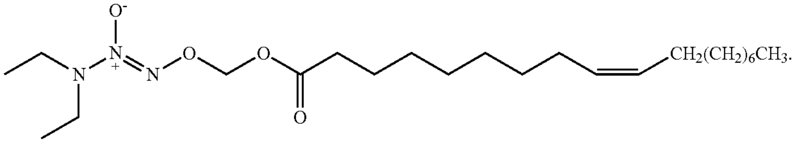

In some embodiments, the compound of Formula I is:

(25)

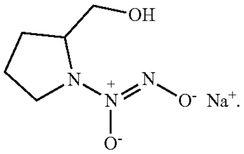

In some embodiments, the compound of Formula I is:

(22)

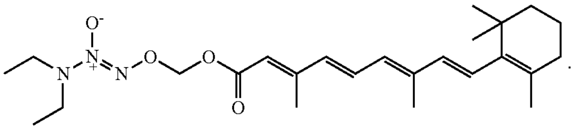

In some embodiments, the compound of Formula I is:

(26)

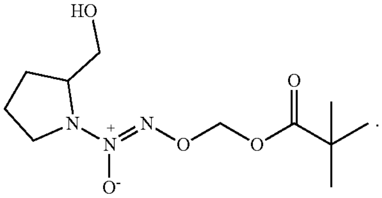

In some embodiments, the compound of Formula I is:

(27)

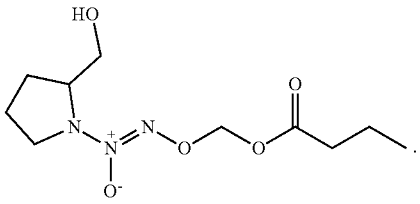

In some embodiments, the compound of Formula I is:

(28)

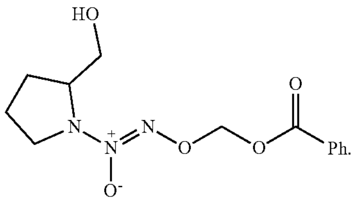

In some embodiments, the compound of Formula I is:

(29)

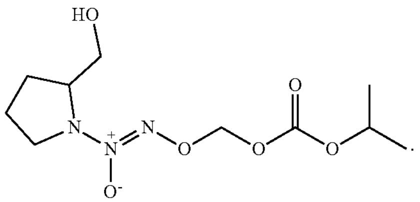

In some embodiments, the compound of Formula I is:

(30)

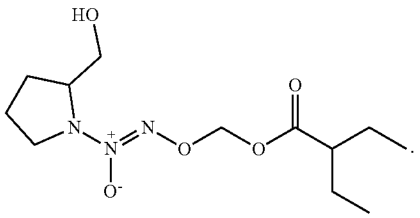

In some embodiments, the compound of Formula I is:

(31)

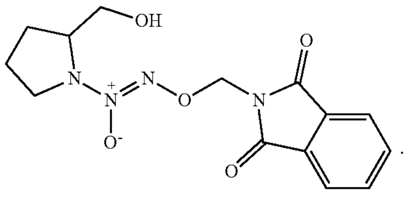

In some embodiments, the compound of Formula I is:

(32)

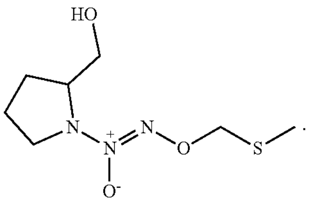

In some embodiments, the compound of Formula I is:

(33)

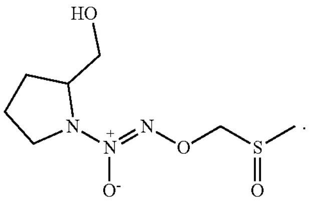

In some embodiments, the present compounds also include one or more of:

(34)

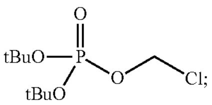

(35)

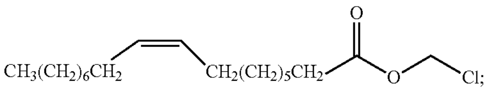

(36)

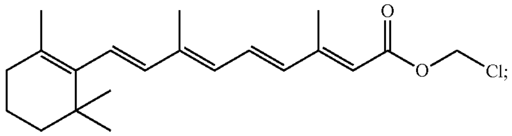

and (37)

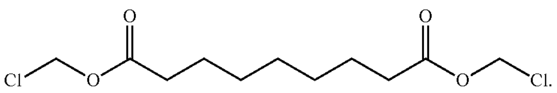

Definitions

The term “alkyl” as used herein, refers to saturated, straight- or branched-chain hydrocarbon radicals. In some embodiments, the alkyl group may consist of 1 to 12 carbon atoms, e.g. 1 carbon atom, 2 carbon atoms, 3 carbon atoms, 4 carbon atoms etc., up to and including 12 carbon atoms. Exemplary alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, septyl, octyl, nonyl and decyl. Examples of such alkyl radicals include but are not limited to methyl, ethyl, propyl, isopropyl, n-butyl, tert-butyl, neopentyl, n-hexyl, n-propyl, n-octyl, n-decyl and n-dodecyl radicals.

The term “alkenyl” as used herein, refers to branched, unbranched or cyclic hydrocarbons, or combination thereof, having one or more carbon-carbon double bond. In some embodiments, the alkenyl group may contain from 2 carbon atoms to 12 carbon atoms, e.g., the alkenyl group may consist of 2 carbon atoms, 3 carbon atoms, 4 carbon atoms etc., up to and including 12 carbon atoms.

The terms "heteroalkyl", "heteroalkenyl" and "heteroalkynyl" include optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given—e.g., $(C_{1-12})$heteroalkyl which refers to number of carbon atoms in the alkyl chain, the range refers to each integer in the given range—e.g., "1 to 12 carbon atoms" in $(C_{1-12})$heteroalkyl means that the heteroalkyl group may contain 1 carbon atom, 2 carbon atoms, 3 carbon atoms, etc., up to and including 12 carbon atoms. A heteroalkyl group may be substituted with one or more substituents which are described herein as suitable substitution groups.

The term "heterocycloalkyl" as used herein, refers to refers to a stable 3- to 18-membered non-aromatic ring radical that comprises two to twelve carbon atoms and from one to six heteroatoms selected from nitrogen, oxygen and sulfur. Whenever it appears herein, a numerical range such as "3 to 18" refers to each integer in the given range—e.g., "3 to 18 ring atoms" means that the heterocycloalkyl group may consist of 3 ring atoms, 4 ring atoms, etc., up to and including 18 ring atoms. Unless stated otherwise specifically in the specification, the heterocycloalkyl radical is a monocyclic, bicyclic, tricyclic or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocycloalkyl moiety is optionally substituted by one or more substituents which are described herein as suitable substitution groups.

The term "aryl," as used herein, refers to a mono-, bicyclic or tricyclic carbocyclic ring system having one, two or three aromatic rings including, but not limited to, phenyl, naphthyl, anthryl, azulyl, tetrahydronaphthyl, indanyl, indenyl and the like.

In various embodiments, the lipid as used herein may be a fatty acid. In some embodiments, the fatty acid may be saturated or unsaturated. Exemplary fatty acids include, without limitation, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, caprylic acid, capric acid, lauric acid, myristic acid, palmitic acid, stearic acid, arachidic acid, behenic acid, lignoceric acid, and cerotic acid. In various embodiments, the lipid may be a glycerolipid such as a triglyceride or a glycosylglycerol. In various embodiments, the lipid may be a glycerophospholipid. Exemplary glycerophospholipids include, without limitation, plasmalogen, phosphatidate, phosphatidylethanolamine, phosphatidylserine, phosphatidylinositol, phosphatidic acid, and phosphatidylcholine. In various embodiments, the lipid may be a sterol lipid such as phytoserol, cholesterol and derivatives, and steroid. In various embodiments, the lipid may be a sphingolipid. Exemplary sphingolipids include, without limitation, sphingoid base, ceramide, sphinomyelin, glycosphingolipid, cerebroside, sulfatide, ganglioside, and inositol-containing ceramide. In various embodiments, the lipid may be a prenol lipid such as an isoprenoid (e.g., carotenoid). In various embodiments, the lipid may be a saccharolipid. In various embodiments, the lipid may be a polyketide. Exemplary polyketides include, without limitation, tetracycline, avermectin, erythromycin and epothilone.

The symbol ∿∿∿, displayed perpendicular to a bond, indicates the point at which the displayed moiety is attached to the remainder of the molecule.

In some embodiments, the definition of terms used herein is according to IUPAC.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J. Pharmaceutical Sciences, 66: 1-19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response and the like, commensurate with a reasonable risk/reward ratio, and effective for their intended use, as well as the zwitterionic forms, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, *Prodrugs as Novel delivery Systems*, Vol. 14 of the A. C. S. Symposium Series and in Edward B. Roche, ed., Bioreversible Carriers in Drug Design, American Pharmaceutical Association and Pergamon Press, 1987, both of which are incorporated by reference herein.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsulate matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, powders, capsules, pills, and granules can be prepared with coatings and shells such as enteric coatings and other coatings well known in the pharmaceutical formulating art. They may optionally contain opacifying agents and can also be of a composition whereby they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention. Accordingly, in various embodiments, the composition may be formulated as a liquid, such as an eye drop, eye wash, gargle, mouth wash, nasal rinse, oral gel, nasal spray, throat spray, or ear drop. In still other embodiments, the composition may take the form of a paste, cream, emulsion, gel, and/or foam for application (e.g., topical application) to the skin.

In some embodiments, the compound of the invention is administered topically, such as by a hydrogel composition. In such embodiments, the composition is effective to ameliorate or reduce (or slow) disease manifestations in the skin, including, for example, lesions, sores, rash, blisters, hives, itch, fibrosis, and calcinosis. Exemplary hydrogel formulations may include, without limitation, polyvinyl alcohol (PVA), polyacrylic acid (PAA), polyvinyl pyrrolidone (PVP), poly(methyl vinyl ether/maleic anhydride), poly (meth)acrylic acid, polethylenglycols (PEG), polyamides, polyacrylic amides, polyethylene glycol (PEG) or copolymers or mixtures thereof.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In various embodiments, the pharmaceutical compositions comprise a compound of the invention at from 1 to 50,000 μM. For example, the pharmaceutical compositions may comprise a compound of the invention at about 1 μM, about 10 μM, about 20 μM, about 30 μM, about 40 μM, about 50 μM, about 60 μM, about 70 μM, about 80 μM, about 90 μM, about 100 μM, about 200 μM, about 300 μM, about 400 μM, about 500 μM, about 600 μM, about 700 μM, about 800 μM, about 900 μM, or about 1,000 μM. In some embodiments, the pharmaceutical composition may comprise a compound of the invention at about 1 mM, about 2 mM, about 3 mM, about 4 mM, about 5 mM, about 6 mM, about 7 mM, about 8 mM, about 9 mM, about 10 mM, about 20 mM, about 30 mM, about 40 mM, or about 50 mM. In some embodiments, including for topical application, the pharmaceutical composition comprises a compound of the invention at from 10 to 2,000 μM, or at from 10 to 2,000 μM, or at from 10 to 1,000 μM.

In various embodiments, the compounds of the invention display biologic effects that can be dose dependent.

Medical Devices

In various embodiments, the present compounds find use in association with a medical device. For instance, and of the present compounds may be bound to a biopolymer, e.g. by formation of a nitric oxide/nucleophile complex in situ on the biopolymer. The present compounds may be attached to an atom in the backbone of a biopolymer, or it may be attached to a group pendant to a biopolymer backbone, or it may simply be entrapped in a biopolymer matrix.

In various embodiments, the compounds of the present invention are associated with a medical device, using non-covalent forms of polymerization including but not limited to: associated with, part of, dispersed within, incorporated with, or contained within a polymer matrix by physical or chemical means and other methods known to those skilled in the art, can provide a localized flux of NO without any deleterious systemic effects. For example, this may be accomplished by mixing a compound of the present invention into a polymer melt comprised of but not limited to poly(ethylene)glycol, poly(caprolactone), poly(urethane), poly(vinyl chloride), and the like, and then casting the polymer into the desired shape, similar to methods described in Biomaterials 2000, 21, 9-21, the entire contents of which are incorporated by reference.

In various embodiments, the present invention relates a device that comes in contact with mammalian tissue in vivo, in vitro, or ex vivo and is associated with a compound of the present invention. Illustrative devices associated with a compound of the present invention include vascular stents, vascular grafts, catheters, wound dressings (e.g. gauzes, tulle, semi-permeable films, hydrocolloid, polyurethane or silicone foams, hydrofibres, and the like), bandages, blood collection bags, blood component storage bags, extracorporeal membrane oxygenation (ECMO) circuits, internal monitoring devices, external monitoring devices.

Further, in some embodiments, one or more therapeutic agents can be incorporated in the medical device comprising the present compounds. For example, In some embodiments, the therapeutic agents can include agents that promote tissue regeneration. In such embodiments, the therapeutic agents can include growth factors including, for example, cytokines and interleukins, extracellular matrix proteins and/or biologically active fragments thereof (e.g., RGD-containing peptides), and blood and serum proteins. These agents can be incorporated into the medical device prior to implantation in a host tissue. Alternatively, the therapeutic agents can be injected into or applied to the medical device already implanted in the host tissue.

Growth factors that can be incorporated into the medical device can include any of a wide range of cell growth factors, angiogenic factors, differentiation factors, cytokines, hormones, and chemokines known in the art. Growth factors can be polypeptides that include the entire amino acid sequence of a growth factor, a peptide that corresponds to only a segment of the amino acid sequence of the native growth factor, or a peptide that is derived from the native sequence that retains the bioactive properties of the native growth factor. The growth factor can be a cytokine or interleukin. Any combination of two or more of the growth factors can be included in the medical device. Examples of relevant factors include vascular endothelial cell growth factors (VEGF) (e.g., VEGF A, B, C, D, and E), platelet-derived growth factor (PDGF), insulin-like growth factor (IGF) I and IGF-II, interferons (IFN) (e.g., IFN-$\alpha$, $\beta$ or $\gamma$), fibroblast growth factors (FGF) (e.g., FGF 1, FGF-2, FGF-3, FGF-4-FGF-10), epidermal growth factor, keratinocyte growth factor, transforming growth factors (TGF) (e.g., TGF$\alpha$ or $\beta$), tumor necrosis factor-a, an interleukin (IL) (e.g., IL-I, IL-2, II-17-IL-18), Osterix, Hedgehogs (e.g., sonic or desert), SOX9, bone morphogenetic proteins (BMPs), in particular, BMP 2, 4, 6, and (BMP-7 is also called OP-1), parathyroid hormone, calcitonin prostaglandins, or ascorbic acid.

Additionally, the present medical devices comprising the present compounds may be associated with various small molecules, or such small molecules find use as combination therapy in the present treatment methods. For instance, the therapeutic agent is, in some embodiments, an antibiotics, which includes, without limitation 1) aminoglycosides, such as gentamycin, kanamycin, neomycin, streptomycin or tobramycin; 2) cephalosporins, such as cefaclor, cefadroxil or cefotaxime; 3) macrolides, such as azithromycin, clarithromycin, or erythromycin; 4) penicillins, such as amoxicillin, carbenicillin or penicillin; 5) peptides, such as bacitracin, polymixin B or vancomycin; 6) quinolones, such as ciprofloxacin, levofloxacin, or enoxacin; 7) sulfonamides, such as sulfamethazole, sulfacetimide; or sulfamethoxazole; 8) tetracyclines, such as doxycycline, minocycline or tetracycline; 8) other antibiotics with diverse mechanisms of action such as rifampin, chloramphenicol, or nitrofuratoin. Further, the therapeutic agent is, in some embodiments, an anti-inflammatory agent, such as, non-steroidal anti-inflammatory drugs (NSAIDs) such as, for example, aspirin, choline and magnesium salicylates, celecoxib, diclofenac potassium, diclofenac sodium, diclofenac sodium with misoprostol, diflunisal, etodolac, fenoprofen, flurbiprofen, ibuprofen, indomethacin, ketoprofen, meclofenamate sodium, mefenamic acid, meloxicam, nabumetone, naproxen, naproxen sodium, oxaprozin, piroxicam, rofecoxib, salsalate, sodium salicylate, sulindac, tolmetin sodium, valdecoxib, any other suitable NSAID or a combination thereof. In some embodiments, the anti-inflammatory agents can include corticosteroids such as, for example, hydrocortisone, hydrocortisone acetate, cortisone acetate, tixocortol pivalate, prednisolone, methylprednisolone, methylprednisolone aceponate, prednisone, triamcinolone acetonide, triamcinolone alcohol, mometasone, mometasone furoate, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-valerate, halometasone, alclometasone dipropionate, betamethasone valerate, betamethasone dipropionate, prednicarbate, clobetasone-17-butyrate, clobetasol-17-propionate, fluocortolone caproate, fluocortolone pivalate, fluprednidene acetate, hydrocortisone-17-butyrate, hydrocortisone-17-aceponate, hydrocortisone-17-buteprate, hydrocortisone valerate, flurandrenolide, triamcinolone acetonide, ciclesonide, halobetasol, diflorasone diacetate, fluocinonide, halicinonide, amcinonide, desoximetasone, fluticasone propionate, betamethasone dipropionate, desonide, alclometasone dipropionate, clobetasol propionate, prednicarbate, any other suitable corticosteroid or a combination thereof.

Methods of Treatment

According to the methods of treatment of the present invention there is administered to the patient a therapeutically effective amount of a compound of the invention, in such amounts and for such time as is necessary to achieve the desired result. By a "therapeutically effective amount" of a compound of the invention is meant a sufficient amount of the compound to treat the disorder, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In various embodiments, the pharmaceutical composition and/or the compounds of the invention may be administered to any tissue, organ, or parts of the body, and which may include the skin, mucus membranes, eyes, ears, nose, sinus cavity, throat, mouth (e.g., gingiva), esophagus, lungs, connective tissue (including skeletal muscles, ligaments, tendons, joints), nervous system, intestinal tract (e.g., colon), urogenital system (including urinary tract or vagina), or the peritoneum. In some embodiments, the route is chosen to administer pharmaceutical composition and/or the compounds to tissues affected by the disease. The pharmaceutical composition and/or the compounds may be administered via any routes of administration which will range from via enteral (oral, gastric and rectal), parenteral (intravenous, intra-arterial, intraosseous, intra-muscular, intrathecal, subcutaneous) or other (sublingually, buccally, rectally, peritoneally, vaginally, intra-articular, by the ocular or otic route, nasally, cutaneously for topical or systemic effect, by inhalation or nebulization, or transdermally) or as an irrigant to one or more tissues or organs (e.g., during an invasive procedure).

In various embodiments, the present compounds, or medical devices comprising the same find use in a variety of treatment methods.

In one embodiment, the present invention relates to a method for delivering nitric oxide to a biological cell, comprising contacting one or more of the present compounds with nitric oxide and contacting the compound bearing nitric oxide with a biological cell to deliver nitric oxide to the biological cell.

In various embodiments, the present invention relates to methods for treating a disorder of nitric oxide dysregulation using the present compounds or a medical device comprising the same.

In various embodiments, the present invention relates to the treatment of various disorders including wound healing (e.g. promoting or enhancing wound healing), cardiovascular dysfunction, circulatory dysfunction, infections (e.g. bacterial, fungal, viral, etc.), ophthalmic dysfunctions, reperfusion, thrombosis or other disorders of nitric oxide dysregulation. In various embodiments, the present invention provides for treatment of erectile dysfunction, vasodilation disorders, cardiovascular disorders (e.g. CVD), endothelial disorders, and wound healing. Providing a therapeutic dose of NO can provide several benefits including reducing microbial infection, reducing inflammation, regulating the formation of collagen, promoting angiogenesis, and treating pulmonary disorders. In addition, a therapeutic dose of NO can be used to supplement or minimize the need for oxygen therapy or rapid descent to lower elevations to treat symptoms of high-altitude sickness.

In various embodiments, the present compounds or medical devices comprising the same find use in improving vascular and/or cellular penetration of drugs.

In various embodiments, the present compositions are used to treat, control or prevent a cardiovascular disease, such as a disease or condition affecting the heart and vasculature, including but not limited to, coronary heart disease (CHD), cerebrovascular disease (CVD), aortic stenosis, peripheral vascular disease, atherosclerosis, arteriosclerosis, myocardial infarction (heart attack), cerebrovascular diseases (stroke), transient ischaemic attacks (TIA), angina (stable and unstable), atrial fibrillation, arrhythmia, vavular disease, and/or heart failure (e.g., congestive heart failure).

In various embodiments, the present compositions are used to treat or prevent one or more metabolic-related disorders. In various embodiments, the present invention is useful for the treatment, controlling or prevention of diabetes, including Type 1 and Type 2 diabetes and diabetes associated with obesity. The compositions and methods of the present invention are useful for the treatment or prevention of diabetes-related disorders, including without limitation diabetic nephropathy, hyperglycemia, impaired glucose tolerance, insulin resistance, obesity, lipid disorders, dyslipidemia, hyperlipidemia, hypertriglyceridemia, hypercholesterolemia, low HDL levels, high LDL levels, atherosclerosis and its sequelae, vascular restenosis, irritable bowel syndrome, inflammatory bowel disease, including Crohn's disease and ulcerative colitis, other inflammatory conditions, pancreatitis, abdominal obesity, neurodegenerative disease, retinopathy, neoplastic conditions, adipose cell tumors, adipose cell carcinomas, such as liposarcoma, prostate cancer and other cancers, including gastric, breast, bladder and colon cancers, angiogenesis, Alzheimer's disease, psoriasis, high blood pressure, Metabolic Syndrome (e.g. a person has three or more of the following disorders: abdominal obesity, hypertriglyceridemia, low HDL cholesterol, high blood pressure, and high fasting plasma glucose), ovarian hyperandrogenism (polycystic ovary syndrome), and other disorders where insulin resistance is a component, such as sleep apnea. The compositions and methods of the present invention are useful for the treatment, control, or prevention of obesity, including genetic or environmental, and obesity-related disorders. The obesity-related disorders herein are associated with, caused by, or result from obesity. Examples of obesity-related disorders include obesity, diabetes, overeating, binge eating, and bulimia, hypertension (e.g., pulmonary hypertension), elevated plasma insulin concentrations and insulin resistance, dyslipidemia, hyperlipidemia, endometrial, breast, prostate, kidney and colon cancer, osteoarthritis, obstructive sleep apnea, gallstones, heart disease, abnormal heart rhythms and arrythmias, myocardial infarction, congestive heart failure, coronary heart disease, sudden death, stroke, polycystic ovary disease, craniopharyngioma, Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are Metabolic Syndrome, insulin resistance syndrome, reproductive hormone abnormalities, sexual and reproductive dysfunction, such as impaired fertility, infertility, hypogonadism in males and hirsutism in females, fetal defects associated with maternal obesity, gastrointestinal motility disorders, such as obesity-related gastro-esophageal reflux, respiratory disorders, such as obesity-hypoventilation syndrome (Pickwickian syndrome), breathlessness, cardiovascular disorders, inflammation, such as systemic inflammation of the vasculature, arteriosclerosis, hypercholesterolemia, lower back pain, gallbladder disease, hyperuricemia, gout, and kidney cancer, and increased anesthetic risk.

In various embodiments, the present compositions are used to treat one or more pulmonary disorders. Exemplary pulmonary disorders include, but are not limited to, pulmonary hypertension, heart and/or lung surgery, asthma, brochospastic diseases, lung ventilation, and sick cell diseases.

In various embodiments, the present compositions are used to treat an intraocular pressure (IOP)-associated condition. In an embodiment, the IOP-associated condition is glaucoma. In various embodiments, the methods of the invention effective treats and/or prevents one or more symptoms associated with glaucoma, including, without limitation, glaucomatous optic nerve damage, visual field defects associated with glaucomatous optic nerve damage, an increase in intraocular pressure, and/or intraocular pressure fluctuations. In an embodiment, methods of the invention are effective in treating primary open-angle glaucoma. In another embodiment, methods of the invention are effective in treating angle-closure glaucoma.

In various embodiments, the present compounds, or medical devices comprising the same find use in methods of treating wounds, including, by way of illustration, acute and chronic wounds, including leg, diabetic and pressure ulcers, burns, and post-surgical wounds. In some embodiments, the present methods are utilized for treating a deep wound, such as a deep dermal ulcer. In another embodiment, the present methods are utilized for treating dry wounds. In another embodiment, the wound is a non-healing wound. In further embodiments, the present methods are utilized for treating decubitus stage I, II, III, or IV ulcer (bedsore), crural ulcers (leg ulcers, open sores on the leg), diabetic ulcers, diabetic foot syndrome or diabetic foot ulcers, skin ulcers, boils, burns (e.g., first and second-degree burns), cuts, skin abrasions, and chronic wounds.

In an embodiment, the present methods are used for treating post-surgical wounds. For example, such wounds may be associated with cardiac surgery, skeletal muscle repair, congenital or incision hernia repair, abdominal surgery, laproscopic incision closure, organ prolapse surgery, gastrointestinal surgery, neurosurgery, severed limb reattachment surgery, open heart surgery, pulmonary surgery, hepatic surgery, renal surgery, ocular surgery, periodontal surgery, orthopedic surgery, cosmetic surgery, and any other surgical procedure or combination thereof.

In various embodiments, methods of the invention promote wound healing. The four types of wound healing are primary, delayed primary, partial thickness, and secondary. Secondary healing, also called healing by contraction, reduces the area of a healing wound. Contraction requires the formation of granulation tissue, which is rich in the blood vessels and fibroblasts which are needed to fill the wound defect. The process involves complex interactions between specialized contracting fibroblasts (myofibroblasts) and the wound matrix. In various embodiments, methods of the invention promote one or more of the four types of wound healing. In various embodiments, methods of the invention affects one or more factors associated with wound healing including, but not limited to, granulation tissue thickness, density of α-smooth muscle actin-positive myofibroblasts, wound healing kinetics, blood vessel density, angiogenesis, and cell proliferation, and tissue ingrowth. In an embodiments, methods of the invention result in a decrease in wound size. In another embodiment, methods of the invention result in an increase in the density of α-smooth muscle actin-positive myofibroblasts. In a further embodiment, methods of the invention promote wound bed remodeling. In some embodiments, methods of the invention promote wound healing by decreasing the time of wound recovery. In some embodiments, methods of the invention promote wound healing by decreasing the inflammatory response. In some embodiments, methods of the invention promote wound healing decreasing or inhibiting scar tissue formation.

In certain embodiments, methods of treating wounds with the medical device comprising the present compounds comprises the step of contacting the wound with the medical devices and, optionally additional steps of, for example, cleaning the wound bed to facilitate wound healing and closure, including, but not limited to: debridement, sharp debridement (surgical removal of dead or infected tissue from a wound), optionally including chemical debriding agents, such as enzymes, to remove necrotic tissue; wound dressings to provide the wound with a moist, warm environment and to promote tissue repair and healing (e.g., wound dressings comprising hydrogels (e.g., AQUASORB®; DUODERM®), hydrocolloids (e.g., AQUACEL®; COMFEEL®), foams (e.g., LYOFOAM®; SPYROSORB®), and alginates (e.g., ALGISITE®; CURASORB®) and administration of growth factors to stimulate cell division and proliferation and to promote wound healing e.g. becaplermin.

In various embodiments, the present methods find use in treating ischemia, by way of non-limiting example, ischemia associated with acute coronary syndrome, acute lung injury (ALI), acute myocardial infarction (AMI), acute respiratory distress syndrome (ARDS), arterial occlusive disease, arteriosclerosis, articular cartilage defect, aseptic systemic inflammation, atherosclerotic cardiovascular disease, autoimmune disease, bone fracture, bone fracture, brain edema, brain hypoperfusion, Buerger's disease, burns, cancer, cardiovascular disease, cartilage damage, cerebral infarct, cerebral ischemia, cerebral stroke, cerebrovascular disease, chemotherapy-induced neuropathy, chronic infection, chronic mesenteric ischemia, claudication, congestive heart failure, connective tissue damage, contusion, coronary artery disease (CAD), critical limb ischemia (CLI), Crohn's disease, deep vein thrombosis, deep wound, delayed ulcer healing, delayed wound-healing, diabetes (type I and type II), diabetic neuropathy, diabetes induced ischemia, disseminated intravascular coagulation (DIC), embolic brain ischemia, frostbite, graft-versus-host disease, hereditary hemorrhagic telengiectasiaischemic vascular disease, hyperoxic injury, hypoxia, inflammation, inflammatory bowel disease, inflammatory disease, injured tendons, intermittent claudication, intestinal ischemia, ischemia, ischemic brain disease, ischemic heart disease, ischemic peripheral vascular disease, ischemic placenta, ischemic renal disease, ischemic vascular disease, ischemia-reperfusion injury, laceration, left main coronary artery disease, limb ischemia, lower extremity ischemia, myocardial infarction, myocardial ischemia, organ ischemia, osteoarthritis, osteoporosis, osteosarcoma, Parkinson's disease, peripheral arterial disease (PAD), peripheral artery disease, peripheral ischemia, peripheral neuropathy, peripheral vascular disease, pre-cancer, pulmonary edema, pulmonary embolism, remodeling disorder, renal ischemia, retinal ischemia, retinopathy, sepsis, skin ulcers, solid organ transplantation, spinal cord injury, stroke, subchondral-bone cyst, thrombosis, thrombotic brain ischemia, tissue ischemia, transient ischemic attack (TIA), traumatic brain injury, ulcerative colitis, vascular disease of the kidney, vascular inflammatory conditions, von Hippel-Lindau syndrome, or wounds to tissues or organs. In an embodiment, the present compounds or medical devices comprising the same find use in treating ischemia-reperfusion injury.

In some embodiments, the present compounds, or medical devices comprising the same find use in the treating infections. In various embodiments, the present invention provides methods of treating bacterial infections. In various embodiments, the bacterial infection is by a gram-positive bacteria, gram-negative bacteria, aerobic and/or anaerobic bacteria. In various embodiments, the bacteria is selected from, but not limited to, *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Nisseria, Baccillus, Bacteroides, Peptococcus, Clostridium, Salmonella, Shigella, Serratia, Haemophilus, Brucella* and other organisms. In some embodiments, the bacteria is selected from, but not limited to, *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* 3452A homology group, *Bacteroides vulgatus, Bacteroides ovalus, Bacte-*

*roides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis*, or *Staphylococcus saccharolyticus*. In various embodiments, the present methods reduce and/or inhibit bacterial adhesion. In various embodiments, the present methods reduce and/or eradicate bacterial biofilms.

In some embodiments, the present invention relates to the treatment of, or a patient having fungal, viral, or parasitic infections. Illustrative infections include, but are not limited to, HIV/AIDS, tuberculosis, osteomyelitis, hepatitis B, hepatitis C, Epstein-Barr virus or parvovirus, and T cell leukemia virus.

In some embodiments, the present compounds, or medical devices comprising the same provide an anti-sceptic or sterilizing effect.

In various embodiments, the present invention provides a method for treating cancer or tumor. As used herein, the terms "cancer" and "tumor" refer to an uncontrolled growth of cells that may interfere with the normal functioning of the bodily organs and systems, including both primary and metastatic cancers or tumors. Primary cancers or tumors that migrate from their original location and seed vital organs can eventually lead to the death of the subject through the functional deterioration of the affected organs. A metastasis is a cancer cell or group of cancer cells, distinct from the primary tumor location, resulting from the dissemination of cancer cells from the primary tumor to other parts of the body. Metastases may eventually result in death of a subject. For example, cancers can include benign and malignant cancers, polyps, hyperplasia, as well as dormant tumors or micrometastasis.

Illustrative cancers that may be treated include, but are not limited to, basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (e.g. that associated with brain tumors), and Meigs' syndrome.

In various embodiments, the present compounds, or medical devices comprising the same find use in promoting gastrointestinal homeostasis. In various embodiments, the present compounds, or medical devices comprising the same find use in preserving gastrointestinal integrity following, for example, injury or drug use. For example, the present methods may preserve, promote, or restore gastrointestinal integrity following damage by drugs such as nonsteroidal anti-inflammatory drugs (NSAIDs).

This invention is further illustrated by the following non-limiting examples

EXAMPLES

The invention will now be described further in detail with respect to specific preferred embodiments by way of examples, it being understood that these are intended to be illustrative only and not limiting of the scope of the invention. Various changes and modifications to the disclosed embodiments will be apparent to those skilled in the art. All parts and percentages recited are by weight unless otherwise specified.

Example 1

Preparation of (Z)-3,3-diethyl-1-hydroxytriaz-1-ene-2-oxide Sodium Salt

The following compound was synthesized:

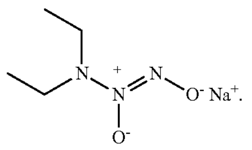

In a pressure bottle 5 ml (48.33 mmol) of diethylamine was added to a solution of 11.8 ml (48.33 mmol) of sodium methoxide (25-30% in methanol) in 146 mL of anhydrous diethyl ether. The mixture was purged with dry nitrogen for 5 min with stirring and then evacuated and back filled with nitrogen three times and finally evacuated and backfilled with NO gas. The mixture was allowed to stir for 5 h under 40 psig NO over which time a white precipitate forms. The vessel was purged by evacuating and backfilling with nitrogen three times before being opened. The product was collected by filtration. The pure white solid was then suspended in diethyl ether (100 ml) and stirred for 15 min. After collection by filtration the pure white solid was dried under vacuum for 2 hours to give the final product.

Yield: 2.4 g (32%)

Example 2

Preparation of (Z)-1-(acetoxymethoxy)-3,3-diethyl-triaz-1-ene-2-oxide (Compound 1)

Bromomethyl acetate (231 mg, 1.5 mmol) was added drop wise to a solution of diethyl NaNOate A (200 mg, 129 mmol)

in acetonitrile at room temperature with stirring. The concentration of the substrate should be 0.6 M in acetonitrile. The reaction was stirred at room temperature under nitrogen for 48 hours. The solid $Na^+Br^-$ was removed using suction filtration. Dichloromethane (1.5 mL) was added and the solution was concentrated to dryness on the rotovap. The resulting solid was dissolved in a minimum amount of dichloromethane and purified using column chromatography (biotage, $SiO_2$, ethyl acetate/hexane gradient)

The structure of the compound was confirmed using $H^-$ NMR.

Yield: 92.1 mg (35%)

Example 3

Preparation of (S,Z)-3-ethyl-10,14,14-trimethyl-9,12-dioxo-6,8,13-trioxa-3,4,5,11-tetraazapentadec-4-ene-4-oxide (Compound 3)

A solution of chloromethyl-Boc-ALA (355 mg, 1.5 mmol) in a minimum amount of acetonitrile was added drop wise to a solution of NaNOate A (200 mg, 1.29 mmol) in acetonitrile at room temperature with stirring. The concentration of the substrate should be 0.6 M in acetonitrile. The reaction was stirred at room temp under nitrogen for 48 hours. The solid $Na^+Br^-$ was removed using suction filtration. Dichloromethane (1.5 mL) was added and the solution was concentrated to dryness on the rotovap. The resulting solid was dissolved in a minimum amount of dichloromethane and purified using column chromatography (biotage, SiO2, ethyl acetate/hexane gradient)

Ran $H^-$ NMR

Boc-Alanine (1.5 g, 8 mmol), tetra-n-butylammonium hydrogen sulfate (0.28 g, 0.8 mmol) and sodium bicarbonate (2.6 g, 31 mmol) were dissolved in water (100 mL). Dichloromethane (100 mL) was added and the resulting mixture was cooled to 0° C. A solution of chloromethylchlorosulfate (1.6 g, 9.7 mmol) in dichloromethane (100 mL) was slowly added under vigorous stirring. The reaction mixture was allowed to reach room temperature and further stirred overnight at this temperature. The organic layer was separated, washed with brine and dried over anhydrous sodium sulfate. The solvent was removed in vacuuo to give the desired product.

Yield: 0.8775 g (46%).

Example 4

Preparation of (Z)-3,3-diethyl-1-((pivaloyloxy)methoxy)triaz-1-ene 2-oxide (Compound 5)

The following compound was synthesized:

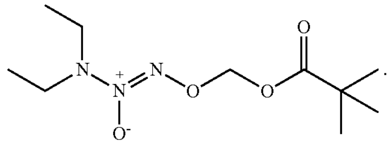

A slurry of NONOate salt I (500 mg, 3.22 mmol) in 13 ml of THF in presence of 15-crown-5 (64 μL, 0.32 mmol) was cooled to 0° C. in an ice bath. To this chloromethyl pivalate (704 mg, 4.67 mmol) was added. The concentration of the substrate should be 0.25 M in tetrahydrofuran. The reaction mixture was allowed to warm up and stirred for 18 h. at room temperature and then 24 h. at 55° C. The solids were removed using suction filtration and concentrated on a rotary evaporator. The resulting mixture was dissolved in a minimum amount of dichloromethane and purified using column chromatography (biotage, $SiO_2$, ethyl acetate/hexane gradient)

The structure of the compound was confirmed using $^1$HNMR.

Yield: 150 mg (18.9%)

General Procedure

A slurry of NONOate salt I (1 eq.) in acetonitrile was cooled to 0° C. in an ice bath, anhydrous sodium carbonate (1.4 eq.) was added followed by chloromethyl derivative (1.2 eq.). The concentration of the substrate should be 0.25 M in acetonitrile. The reaction mixture was allowed to warm up to room temperature and stirred for 18 h. The solids were removed using suction filtration and concentrated on a rotary evaporator. The resulting mixture was dissolved in a minimum amount of dichloromethane and purified using column chromatography (biotage, $SiO_2$, ethyl acetate/hexane gradient)

The above general procedure was used to prepare the following examples. In all cases the structure of the compound was confirmed using $^1$HNMR.

Example 5

(Z)-1-((butyryloxy)methoxy)-3,3-diethyltriaz-1-ene 2-oxide (Compound 6)

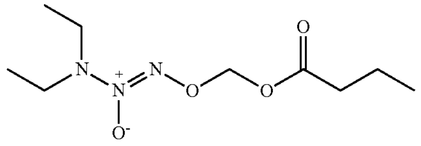

Yield: 0.8%

Example 6

(Z)-1-((benzoyloxy)methoxy)-3,3-diethyltriaz-1-ene 2-oxide (Compound 7)

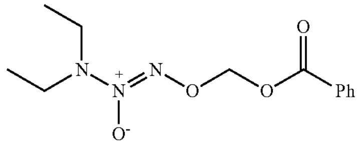

Yield: 4.3%

Example 7

(Z)-3,3-diethyl-1-((isobutyryloxy)methoxy)triaz-1-ene 2-oxide (Compound 8)

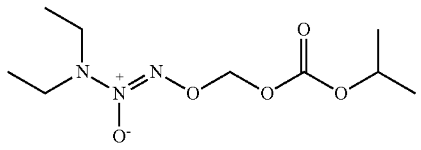

Yield: 1.6%

Example 8

(Z)-3,3-diethyl-1-(((2-ethylbutanoyl)oxy)methoxy)triaz-1-ene 2-oxide (Compound 9)

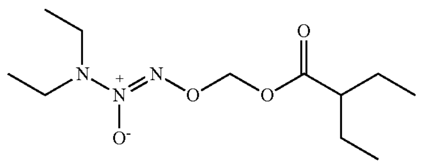

Yield: 2.3%

Example 9

(Z)-3-ethyl-10,10,14,14-tetramethyl-9,12-dioxo-6,8,13-trioxa-3,4,5,11-tetraazapentadec-4-ene 4-oxide (Compound 10)

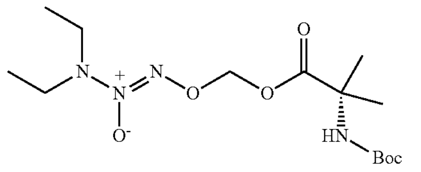

Yield: 4.8%

Example 10

(S,Z)-3-ethyl-10-isopropyl-14,14-dimethyl-9,12-dioxo-6,8,13-trioxa-3,4,5,11-tetraazapentadec-4-ene 4-oxide (Compound 4)

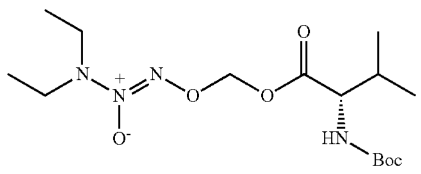

Yield: 3.6%

Chloromethyl Boc-Valine (1.73 g, 8 mmol), tetra-n-butylammonium hydrogen sulfate (0.28 g, 0.8 mmol) and sodium bicarbonate (2.6 g, 30.90 mmol) were dissolved in water (100 mL). Dichloromethane (100 mL) was added and the resulting mixture was cooled to 0° C. A solution of chloromethylchlorosulfate (1.6 g, 9.70 mmol) in dichloromethane (100 mL) was slowly added under vigorous stirring. The reaction mixture was allowed to reach room temperature and further stirred overnight at this temperature. The organic layer was separated, washed with brine and dried over anhydrous sodium sulfate. The solvent was removed in vacuuo to give the desired product.

Yield: 1.4 g (67%)

Example 11

(Z)-3,3-diethyl-1-((undecanoyloxy)methoxy)triaz-1-ene 2-oxide (Compound 11)

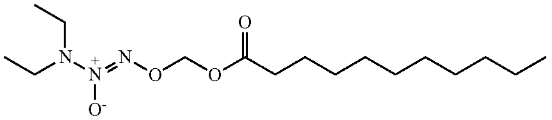

Yield: 4.4%

Example 12

(Z)-3-ethyl-7,11,11-trimethyl-9-oxo-6,8,10-trioxa-3,4,5-triazadodec-4-ene 4-oxide (Compound 12)

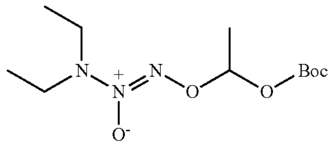

Yield: 1.6%

Example 13

(Z)-3-ethyl-7,11-dimethyl-9-oxo-6,8,10-trioxa-3,4,5-triazadodec-4-ene 4-oxide (Compound 13)

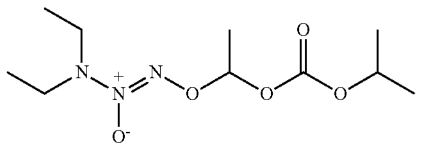

Yield: 1.3%

Example 14

(Z)-1-((1,3-dioxoisoindolin-2-yl)methoxy)-3,3-diethyltriaz-1-ene 2-oxide (Compound 14)

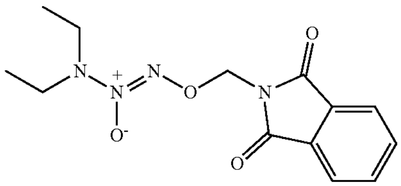

Yield: 20.4%

Example 15

Preparation of (Z)-1-(((2-amino-2-methylpropanoyl)oxy)methoxy)-3,3-diethyltriaz-1-ene 2-oxide (Compound 15)

The following compound was synthesized:

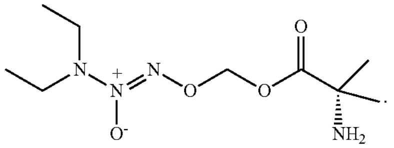

A solution of (Z)-3-ethyl-10,10,14,14-tetramethyl-9,12-dioxo-6,8,13-trioxa-3,4,5,11-tetraazapentadec-4-ene 4-oxide (14.6 mg, 0.04 mmol) in 4N HCl/dioxane (2.0 mL) was stirring at r.t. for 25 min and then evaporated under reduced pressure. To this diethyl ether was added three times and evaporated. Final crude mixture was suspended in diethyl ether, filtered, washed with diethyl ether and dried in vacuum.

The structure of the compound was confirmed using $^1$HNMR.

Yield: 8 mg (76%)

Example 16

Preparation of (S,Z)-1-(((2-amino-3-methylbutanoyl)oxy)methoxy)-3,3-diethyltriaz-1-ene 2-oxide (Compound 16)

The following compound was synthesized:

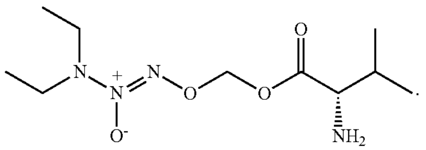

A solution of (S,Z)-3-ethyl-10-isopropyl-14,14-dimethyl-9,12-dioxo-6,8,13-trioxa-3,4,5,11-tetraazapentadec-4-ene 4-oxide (8 mg, 0.02 mmol) in 4N HCl/dioxane (1.5 mL) was stirring at r.t. for 25 min and then evaporated under reduced pressure. To this diethyl ether was added three times, evaporated and dried in vacuum overnight. To this oily mixture diethyl ether (1 mL) was added and stirred at r.t. This allowed precipitation of the product which was filtered, washed with diethyl ether and dried in vacuum.

The structure of the compound was confirmed using $^1$HNMR.

Yield: 3.4 mg (59%)

Example 17

Preparation of (Z)-1-(((di-tert-butoxyphosphoryl)oxy)methoxy)-3,3-diethyltriaz-1-ene-2-oxide (Compound 2)

The following compound was synthesized:

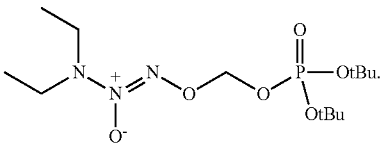

A slurry of NONOate salt I (200 mg, 1.29 mmol) and sodium carbonate (205 mg, 1.93 mmol) were suspended in 3 mL of tetrahydrofuran and cooled to 0° C. Di-tert-butyl chloromethyl phosphate (500 mg, 1.93 mmol) was added, followed by the addition of 2.5 mL N,N-dimethylformamide and sodium iodide (290 mg, 1.93 mmol). The reaction mixture was allowed to warm to room temperature and stirred for 18 h. The mixture was concentrated on a rotary evaporator, treated with water and extracted with ethyl acetate. The combined organic layers were dried over sodium sulfate and evaporated. The resulting mixture was dissolved in a minimum amount of dichloromethane and purified using column chromatography (biotage, $SiO_2$, ethyl acetate/hexane gradient)

The structure of the compound was confirmed using $^1$HNMR.

Yield: 32.44 mg (7%)

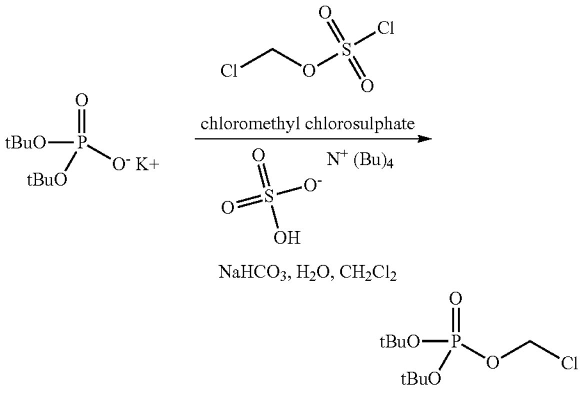

Potassium ditertiarybutyl phosphate (2 g, 8 mmol), tetra-n-butylammonium hydrogen sulfate (0.28 g, 0.8 mmol) and sodium bicarbonate (2.6 g, 30.90 mmol) were dissolved in water (100 mL). Dichloromethane was added (100 mL) and the resulting mixture was cooled down to 0° C. A solution of chloromethylchlorosulfate (1.6 g, 9.70 mmol) in dichloromethane (100 mL) was slowly added under vigorous stirring. The reaction mixture was allowed to reach room temperature and further stirred overnight at this temperature.

The organic layer was separated, washed with brine and dried over anhydrous sodium sulfate. The solvent was removed in vacuuo to give the product.

The structure of the compound was confirmed using LC/MS.

Product was used directly without purification.

Yield: 1.2 g (57.6%)

Example 18

Preparation of (Z)-3,3-diethyl-1-(oxiran-2-yl-methoxy)triaz-1-ene 2-oxide (Compound 17)

The following compound was synthesized:

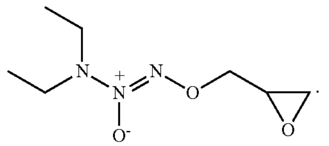

A slurry of NONOate salt I (200 mg, 1.29 mmol) and sodium hydroxide (124 mg, 3.09 mmol) were suspended in 3 mL of THF and cooled to 0° C. Epichlorohydrin (121 μL, 1.54 mmol) was added, followed by the addition of 2.5 mL N,N-dimethylformamide and sodium iodide (212 mg, 1.41 mmol). The reaction mixture was allowed to warm to room temperature and stirred for 18 h. The mixture was concentrated on a rotary evaporator, treated with water and extracted with ethyl acetate. The combined organic layers were dried over sodium sulfate and evaporated. The resulting mixture was dissolved in a minimum amount of dichloromethane and purified using column chromatography (biotage, $SiO_2$, ethyl acetate/hexane gradient)

The structure of the compound was confirmed using $^1$HNMR.

Yield: 6.8 mg (2.7%)

Example 19

Preparation of (Z)-3,3-diethyl-1-((methylthio) methoxy)triaz-1-ene 2-oxide (Compound 18)

The following compound was synthesized:

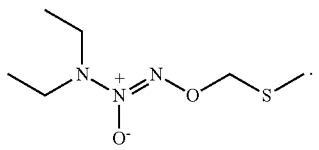

A slurry of NONOate salt I (200 mg, 1.29 mmol) and sodium carbonate (136 mg, 1.29 mmol) were suspended in 3 mL of THF and cooled to 0° C. Chloromethyl methylsulfide (139 μL, 1.67 mmol) was added, followed by the addition of 2.5 mL N,N-dimethylformamide. After 5 min, the ice bath was removed and catalytic amount of sodium iodide was added. The reaction was allowed to stir at room temperature overnight. The pink reaction was quenched with water and extracted five times with n-butanol. The combined organic layer was washed with water and evaporated under reduced pressure, which also removed the pink color. The resulting mixture was dissolved in a minimum amount of dichloromethane and purified using column chromatography (biotage, $SiO_2$, ethyl acetate/hexane gradient).

The structure of the compound was confirmed using $^1$HNMR.

Yield: 59 mg (23.6%)

Example 20

Preparation of (Z)-3,3-diethyl-1-((methylsulfinyl) methoxy)triaz-1-ene 2-oxide (Compound 19)

The following compound was synthesized:

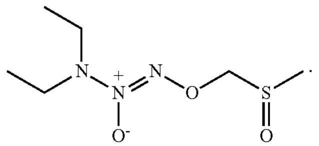

m-Chloroperbenzoic acid (33.1 mg, 0.19 mmol) was added to the solution of (Z)-3,3-diethyl-1-((methylthio) methoxy)triaz-1-ene 2-oxide (30.9 mg, 0.16 mmol) in 1.5 ml of dichloromethane. The reaction was allowed to stir overnight. Resulting mixture was directly purified using column chromatography (biotage, $SiO_2$, methanol/dichloromethane gradient).

The structure of the compound was confirmed using $^1$HNMR.

Yield: 28.9 mg (86.3%)

Example 21

Preparation of (Z)-3,3-diethyl-1-((methylsulfonyl) methoxy)triaz-1-ene 2-oxide (Compound 20)

The following compound was synthesized:

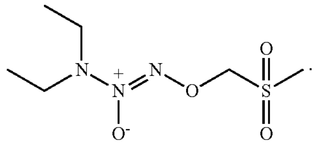

m-Chloroperbenzoic acid (120.6 mg, 0.69 mmol) was added to the solution of (Z)-3,3-diethyl-1-((methylthio) methoxy)triaz-1-ene 2-oxide (45 mg, 0.23 mmol) in 2 ml of dichloromethane. The reaction was allowed to stir overnight. Resulting mixture was directly purified using column chromatography (biotage, $SiO_2$, ethyl acetate/hexane gradient).

The structure of the compound was confirmed using $^1$HNMR.

Yield: 40 mg (76%)

Example 22

Preparation of (Z)-3,3-diethyl-1-((oleoyloxy)methoxy)triaz-1-ene 2-oxide (Compound 21)

The following compound was synthesized:

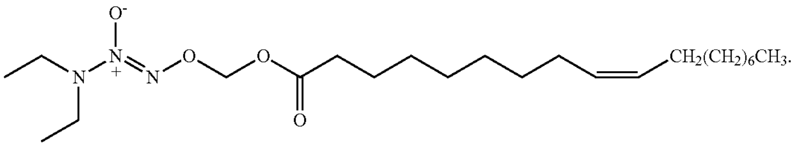

A slurry of NONOate salt 1 (200 mg, 1.29 mmol) in acetonitrile was cooled to 0° C. in an ice bath, anhydrous sodium carbonate (191.4 mg, 1.8 mmol) was added followed by chloromethyl oleate (511.74 mg, 1.54 mmol). The concentration of the substrate should be 0.25 M in acetonitrile. The reaction mixture was allowed to warm to room temperature and stirred for 18 h. The solids were removed using suction filtration and concentrated on a rotary evaporator. The resulting mixture was dissolved in a minimum amount of dichloromethane and purified using column chromatography (biotage, $SiO_2$, ethyl acetate/hexane gradient)

The structure of the compound was confirmed using $^1$HNMR.

Yield: 34.48 mg (6.2%)

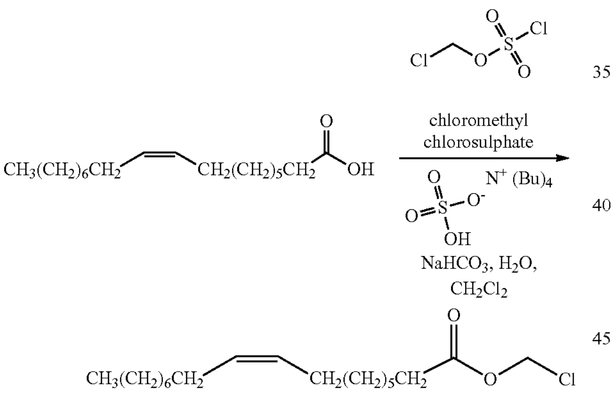

Oleic acid (3 g, 10.6 mmol), tetra-n-butylammonium hydrogen sulfate (0.36 g, 1.06 mmol) and sodium bicarbonate (3.45 g, 40.4 mmol) were dissolved in water (100 mL). Dichloromethane was added (100 mL) and the resulting mixture was cooled down to 0° C. A solution of chloromethylchlorosulfate (2.12 g, 12.80 mmol) in dichloromethane (100 mL) was slowly added under vigorous stirring. The reaction mixture was allowed to reach room temperature and further stirred overnight at this temperature. The organic layer was separated, washed with brine and dried over anhydrous sodium sulfate. Solvent was removed on a rotary evaporator. The resulting mixture was dissolved in a minimum amount of dichloromethane and purified using column chromatography (biotage, $SiO_2$, ethyl acetate/hexane gradient).

The structure of the compound was confirmed using $^1$HNMR.

Yield: 2.4 g (68%)

Example 23

Preparation of (Z)-1-((((2E,4E,6E,8E)-3,7-dimethyl-9-(2,6,6-trimethylcyclohex-1-en-1-yl)nona-2,4,6,8-tetraenoyl)oxy)methoxy)-3,3-diethyltriaz-1-ene 2-oxide (Compound 22)

The following compound was synthesized:

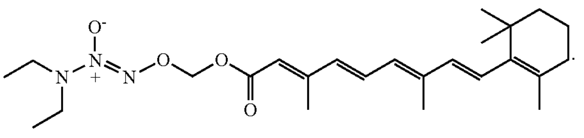

A slurry of NONOate salt I (200 mg, 1.29 mmol) in acetonitrile was cooled to 0° C. in an ice bath, anhydrous sodium carbonate (191 mg, 1.8 mmol) was added followed by (2E,4E,6E,8E)-chloromethyl 3,7-dimethyl-9-(2,6,6-trimethylcyclohex-1-en-1-yl)nona-2,4,6,8-tetraenoate (540 mg, 1.54 mmol). The concentration of the substrate should be 0.25 M in acetonitrile. The reaction mixture was allowed to warm to room temperature and stirred for 18 h. The solids were removed using suction filtration and concentrated on a rotary evaporator. The resulting mixture was dissolved in a minimum amount of dichloromethane and purified using column chromatography (biotage, $SiO_2$, ethyl acetate/hexane gradient)

The structure of the compound was confirmed using $^1$HNMR.

Yield: 6 mg (1%)

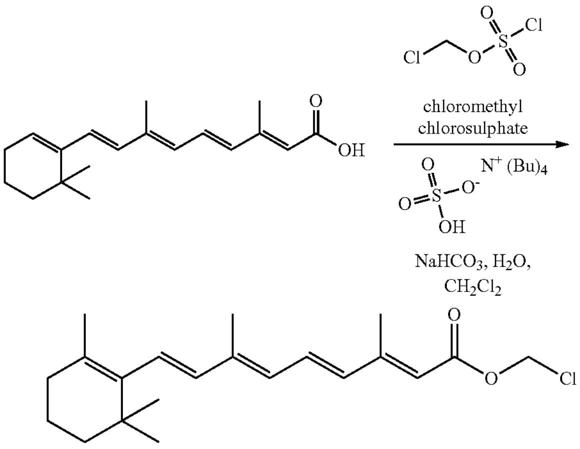

Retinoic acid (2 g, 6.65 mmol), tetra-n-butylammonium hydrogen sulfate (0.22 g, 0.66 mmol) and sodium bicarbonate (2.23 g, 26.62 mmol) were dissolved in water (100 mL). Dichloromethane was added (100 mL) and the resulting mixture was cooled down to 0° C. A solution of chloromethylchlorosulfate (1.32 g, 8 mmol) in dichloromethane (100 mL) was slowly added under vigorous stirring. The reaction mixture was allowed to reach room temperature and further stirred overnight at this temperature. The organic layer was separated, washed with brine and dried over anhydrous sodium sulfate. The solvent was removed in vacuuo to give the product.

The structure of the compound was confirmed using $^1$HNMR.

Product was used directly without purification.

Yield: 2 g (86%)

Example 24

(Z)-1-chloro-17-ethyl-3,11-dioxo-2,12,14-trioxa-15,16,17-triazanonadec-15-ene 16-oxide (Compound 23)

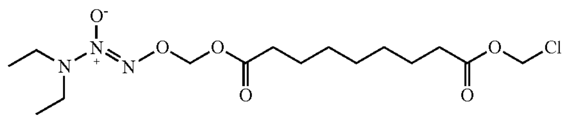

A slurry of NONOate salt I (707 mg, 4.56 mmol) in acetonitrile was cooled to 0° C. in an ice bath, anhydrous sodium carbonate (726 mg, 6.85 mmol) was added followed by bis(chloromethyl) nonanedioate (434.25 mg, 1.52 mmol). The concentration of the substrate should be 0.25 M in acetonitrile. The reaction mixture was allowed to warm to room temperature and stirred for 48 h. The solids were removed using suction filtration and concentrated on a rotary evaporator. The resulting mixture was dissolved in a minimum amount of dichloromethane and purified using column chromatography (biotage, $SiO_2$, ethyl acetate/hexane gradient).

The structure of the compound was confirmed using $^1$HNMR.

Yield: 52 mg (8.9%)

Example 25

(4Z,21Z)-3,23-diethyl-9,17-dioxo-6,8,18,20-tetraoxa-3,4,5,21,22,23-hexaazapentacosa-4,21-diene 4,22-dioxide (Compound 24)

A slurry of NONOate salt I (707 mg, 4.56 mmol) in acetonitrile was cooled to 0° C. in an ice bath, anhydrous sodium carbonate (726 mg, 6.85 mmol) was added followed by bis(chloromethyl) nonanedioate (434.25 mg, 1.52 mmol). The concentration of the substrate should be 0.25 M in acetonitrile. The reaction mixture was allowed to warm to room temperature and stirred for 48 h. The solids were removed using suction filtration and concentrated on a rotary evaporator. The resulting mixture was dissolved in a minimum amount of dichloromethane and purified using column chromatography (biotage, $SiO_2$, ethyl acetate/hexane gradient).

The structure of the compound was confirmed using $^1$HNMR.

Yield: 9 mg (1.2%)

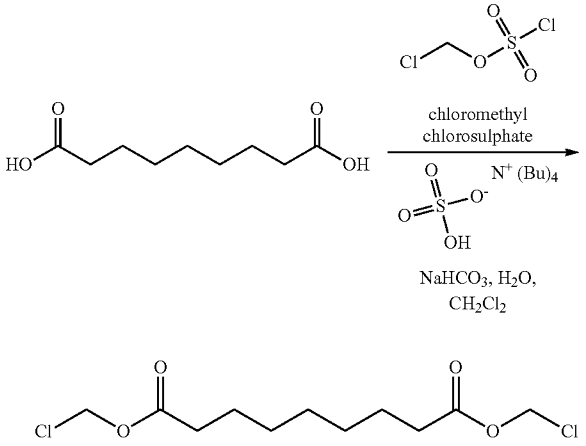

Azelaic acid (4 g, 21.25 mmol), tetra-n-butylammonium hydrogen sulfate (1.44 g, 4.25 mmol) and sodium bicarbonate (14.28 g, 170 mmol) were dissolved in water (200 mL). Dichloromethane was added (200 mL) and the resulting mixture was cooled down to 0° C. A solution of chloromethylchlorosulfate (8.48 g, 51 mmol) in dichloromethane (200 mL) was slowly added under vigorous stirring. The reaction mixture was allowed to reach room temperature and further stirred overnight at this temperature. The organic layer was separated, washed with brine and dried over anhydrous sodium sulfate. Solvent was removed on a rotary evaporator. The resulting mixture was dissolved in a minimum amount of dichloromethane and purified using column chromatography (biotage, $SiO_2$, ethyl acetate/hexane gradient).

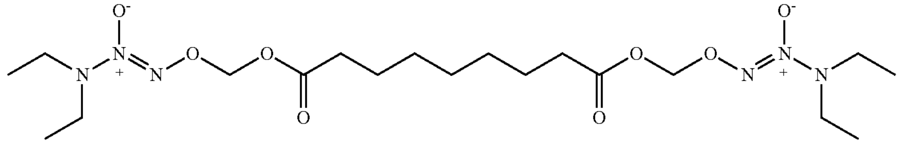

The structure of the compound was confirmed using $^1$HNMR.

Yield: 434.25 mg (7%)

Example 26

Preparation of (Z)-2-hydroxy-1-(2-(hydroxymethyl) pyrrolidin-1-yl)diazene Oxide Sodium Salt (Compound 25)

The following compound was synthesized:

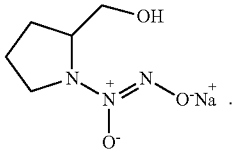

In a pressure bottle 4.8 ml (47.45 mmol) of prolinol was added to a solution of 9.5 ml (52.75 mmol) of sodium methoxide (25-30% in methanol) in 50 mL of anhydrous diethyl ether. The mixture was purged with dry nitrogen for 5 min with stirring and then evacuated and back filled with nitrogen three times and finally evacuated and backfilled with NO gas. The mixture was allowed to stir for 6 h under 60 psig NO over which time a white precipitate forms. The vessel was purged by evacuating and backfilling with nitrogen three times before being opened. The product was collected by filtration. The pure white solid was then suspended in diethyl ether (100 ml) and stirred for 15 min. After collection by filtration the pure white solid was dried under vacuum for 2 hours to give the final product.

Yield: 8.2 g (94%)

General Procedure

A slurry of NONOate salt XIII (1 eq.) in tetrahydrofuran in presence of 15-crown-5 (0.1 eq.) was cooled to 0° C. in an ice bath. To this chloromethyl derivative (1.4 eq.) was added. The concentration of the substrate should be 0.25 M in tetrahydrofuran. The reaction mixture was allowed to warm up and stirred for 18 h. at room temperature. The solids were removed using suction filtration and concentrated on a rotary evaporator. The resulting mixture was dissolved in a minimum amount of dichloromethane and purified using column chromatography (biotage, $SiO_2$, ethyl acetate/hexane gradient)

The above general procedure was used to prepare the following examples. In all cases the structure of the compound was confirmed using $^1$HNMR.

Example 27

(Z)-1-(2-(hydroxymethyl)pyrrolidin-1-yl)-2-((pivaloyloxy)methoxy)diazene oxide (Compound 26)

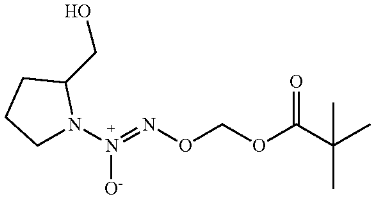

Yield: 3.3%

Example 28

(Z)-2-((butyryloxy)methoxy)-1-(2-(hydroxymethyl) pyrrolidin-1-yl)diazene oxide (Compound 27)

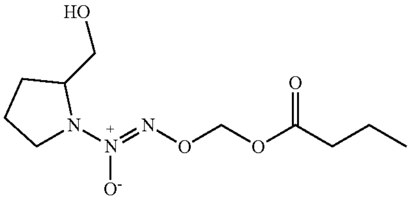

Yield: 1.8%

Example 29

(Z)-2-((benzoyloxy)methoxy)-1-(2-(hydroxymethyl) pyrrolidin-1-yl)diazene oxide (Compound 28)

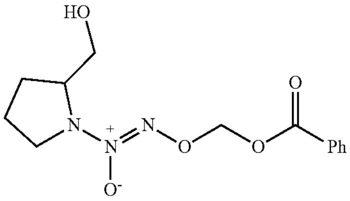

Yield: 4.5%

Example 30

(Z)-1-(2-(hydroxymethyl)pyrrolidin-1-yl)-2-(((isopropoxycarbonyl)oxy)methoxy)diazene oxide (Compound 29)

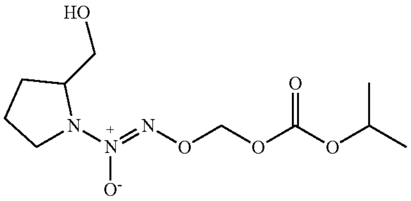

Yield: 4.2%

Example 31

(Z)-2-(((2-ethylbutanoyl)oxy)methoxy)-1-(2-(hydroxymethyl)pyrrolidin-1-yl)diazene oxide (Compound 30)

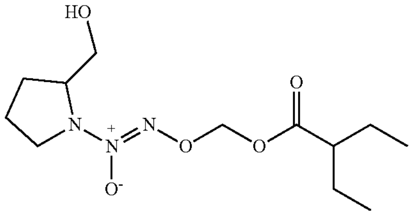

Yield: 3.3%

Example 32

(Z)-2-((1,3-dioxoisoindolin-2-yl)methoxy)-1-(2-(hydroxymethyl)pyrrolidin-1-yl)diazene oxide (Compound 31)

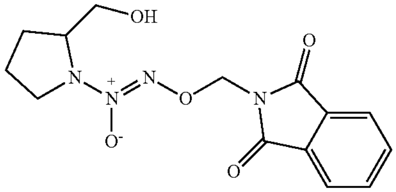

Yield: 49.8%

Example 33

Preparation of (Z)-1-(2-(hydroxymethyl)pyrrolidin-1-yl)-2-((methylthio)methoxy)diazene oxide (Compound 32)

The following compound was synthesized:

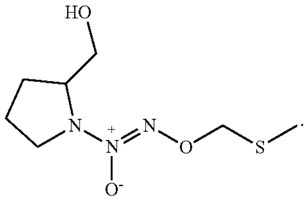

A slurry of NONOate salt XIII (400 mg, 2.18 mmol) and sodium carbonate (231 mg, 2.18 mmol) were suspended in 4.8 mL of THF and cooled to 0° C. Chloromethyl methylsulfide (236.58 μL, 2.84 mmol) was added, followed by the addition of 2 mL of N,N-dimethylformamide. After 5 min, the ice bath was removed and catalytic amount of sodium iodide was added. The reaction was allowed to stir at room temperature overnight. The reaction was treated with water and extracted with dichloromethane. The combined organic layers were washed with water and evaporated under reduced pressure. The resulting mixture was dissolved in a minimum amount of dichloromethane and purified using column chromatography (biotage, $SiO_2$, ethyl acetate/hexane gradient).

The structure of the compound was confirmed using $^1$HNMR.

Yield: 175.3 mg (36.2%)

Example 34

Preparation of (Z)-1-(2-(hydroxymethyl)pyrrolidin-1-yl)-2-((methylsulfinyl)methoxy)diazene oxide (Compound 33)

The following compound was synthesized:

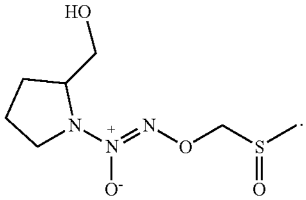

m-Chloroperbenzoic acid (47.2 mg, 0.27 mmol) was added to the solution of (Z)-3,3-diethyl-1-((methylthio)methoxy)triaz-1-ene 2-oxide (50.4 mg, 0.22 mmol) in 2.5 ml of dichloromethane. The reaction was allowed to stir overnight. Resulting mixture was directly purified using column chromatography (biotage, $SiO_2$, methanol/dichloromethane gradient).

The structure of the compound was confirmed using $^1$HNMR.

Yield: 31 mg (57%).

Example 35

NO Release Kinetics

Compounds were tested for release of NO in PBS versus rat plasma using the Griess reaction. The Griess reaction works by the colorimetric measurement of nitrite levels which is the primary breakdown product of NO. To determine stability, as well as NO release behavior in a biological environment, the compounds were tested for NO release in both PBS and rat plasma at 37° C.

Figure 2:
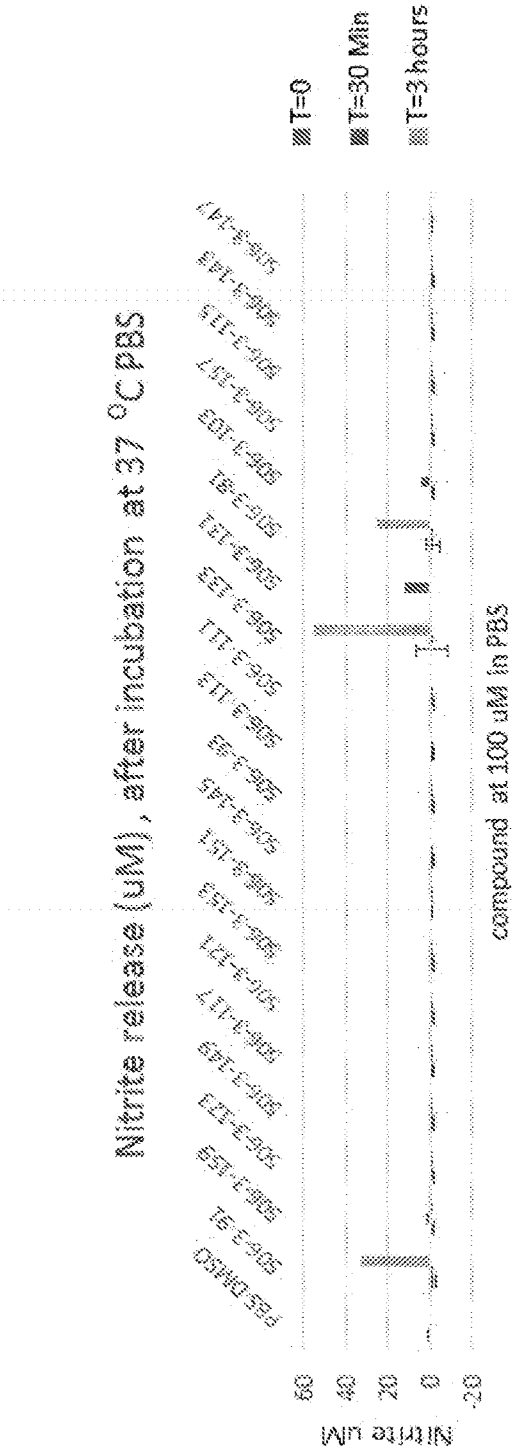
FIG. 2, panel A, shows NO release by various disclosed compounds (X axis) at 100 μM in PBS. The compounds were dissolved in DMSO and added to PBS and then incubated at 37° C. NO release was measured using the Griess reaction at t=0, 30 minutes, and 3 hours. NO production in this assay was an indication of the hydrolytic instability of the capping group. Panel B shows NO release by the compounds (X axis) at 100 μM in rat plasma. Compounds were dissolved in DMSO and added to rat plasma and then incubated at 37° C. NO release was measured using the Griess reaction at t=0, 30 minutes, and 3 hours. Differences in the amount and rate of NO release reflect the kinetics of hydrolysis of the capping groups by proteases endogenous to the rat plasma. This experiment reflected the ability of compounds to release NO in vivo. For both panels A and B, the compounds tested are labelled as: 506-3-91 is Compound 31, 506-3-159 is Compound 33, 506-3-123 is Compound 32, 506-3-149 is Compound 30, 506-3-117 is Compound 26506-3-121 is Compound 29, 506-3-153 is Compound 27, 506-3-151 is Compound 28, 506-3-145 is Compound 7, 506-3-93 is Compound 10, 506-3-113 is Compound 4, 506-3-111 is Compound 11, 506-3-133 is Compound 12, 506-3-131 is Compound 13, 506-3-81 is Compound 14, 506-3-103 is Compound 18, 506-3-157 is Compound 19, 506-3-115 is Compound 9, 506-3-143 is Compound 6, and 506-3-147 is Compound 8. For all compounds, three time points are shown (left to right for each labelled compound): 0 time point, 30 minutes time point, and 3 hours time point.
Figure 2:
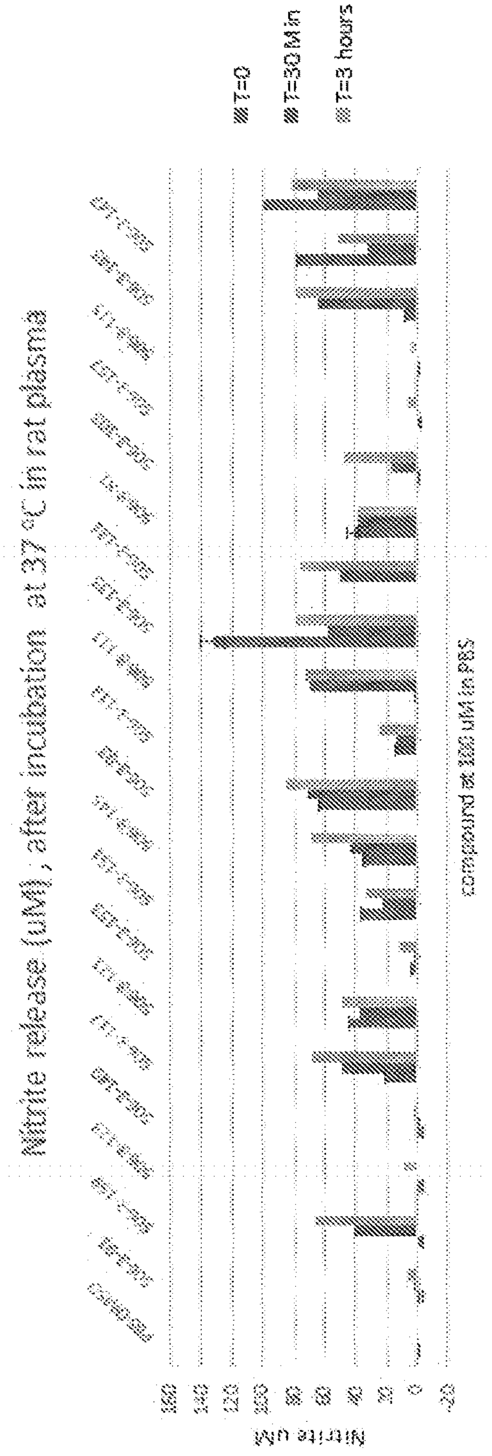

FIG. 1, panels A and B, show differential NO release by 5 μM of the compounds in PBS versus Rat Plasma at time points 0 and 3 hours. Generally, release of NO was minimal in PBS and generally equivalent at time 0 and time 30 minutes. Release of NO was generally higher in plasma than PBS at both time points and much higher in plasma at 3 hours than at 30 min. Differential release rates could be seen for different compounds indicating differential susceptibility to plasma initiated NO release depending on structure Additional experiments were carried out to test the NO release capability of 100 μM of the compounds in PBS versus Rat Plasma. In these experiments, NO release kinetics was explored by taking readings at 0 minutes, 30 minutes, and 3 hours. The results are shown in FIG. 2, panels A and B. From these studies, the compounds were classified and ranked based on their NO release behavior as shown in the Table below.

| compound | Release Behavior |
|---|---|
| 506-3-91 | unstable |
| 506-3-159 | slow/low release |
| 506-3-123 | slow/low release |
| 506-3-149 | slow onset |
| 506-3-117 | steady |
| 506-3-121 | slow/low release |
| 506-3-153 | steady/low |
| 506-3-151 | slow onset |
| 506-3-145 | steady |
| 506-3-93 | slow/low release |
| 506-3-113 | slow onset |
| 506-3-111 | quick/long release |
| 506-3-133 | unstable |
| 506-3-131 | steady/low |
| 506-3-81 | unstable |
| 506-3-103 | slow/low release |
| 506-3-157 | slow/low release |
| 506-3-115 | slow onset |
| 506-3-143 | intermediate |
| 506-3-147 | steady |

As provided above: 506-3-91 is Compound 31, 506-3-159 is Compound 33, 506-3-123 is Compound 32, 506-3-149 is Compound 30, 506-3-117 is Compound 26506-3-121 is Compound 29, 506-3-153 is Compound 27, 506-3-151 is Compound 28, 506-3-145 is Compound 7, 506-3-93 is Compound 10, 506-3-113 is Compound 4, 506-3-111 is Compound 11, 506-3-133 is Compound 12, 506-3-131 is Compound 13, 506-3-81 is Compound 14, 506-3-103 is Compound 18, 506-3-157 is Compound 19, 506-3-115 is Compound 9, 506-3-143 is Compound 6, and 506-3-147 is Compound 8.

All together, these results indicate that the compounds of the invention can be activated for NO release upon exposure to plasma or wound exudate. Based on the ranking provided above, as well as considerations of structure and chemical stability, the compounds 506-3-149, 506-3-151, 506-3-145, 506-3-111, and 506-3-147 were selected for stability testing in a hydrogel formulation as described in the Example below.

Example 36

Generation and Characterization of Gel Formulations

The compounds of the invention were formulated into a suitable hydrogel matrix so as to facilitate the use of these compounds on wounds. Two different hydrogel formulations were initially examined. The first hydrogel was poly vinyl alcohol (PVA) at 15% (w/v) in water. The second hydrogel was polyacrylic acid (PAA) at 7% (w/v) in water. To prepare these gels, the polymers were heated in aqueous solution until they dissolved. This was followed by cooling and formulation. The PAA polymer required titration with 0.1 N NaOH to neutralize the gel after dissolution. Both gel formulations were assayed for viscosity, stability and general suitableness for use in animal studies. In this regard, the PVA gel showed superior viscosity and handling characteristics.

The compounds of the invention were dissolved in the gels and assayed for NO production. Based on the studies, compound 506-3-111, formulated in 15% PVA in water, was selected for use in further animal studies.

With respect to compound 506-3-111 specifically, it was observed that the pure compound was stable for over one year. Additional studies are performed to study the long term stability of the compound as formulated in the gel along with its NO release properties.

All together, these studies indicated that the gel formulations were stable and could be used to formulate the NO release compounds without the need to initiate NO release ex vivo. Specifically, these gel formulations readily allowed NO release upon contact with plasma or wound exudate.

Example 37

Wound Healing Studies

A murine diabetic wound model for utilized to test the ability of the gel formulation of the invention to accelerate wound healing. Specifically, diabetic Lep/r-db/db mice were used to study the effects of the gel formulation on granulation tissue thickness, density of α-smooth muscle actin-positive myofibroblasts, wound healing kinetics, blood vessel density, cell proliferation, and tissue ingrowth.

In the US alone, 25.8 million people have diabetes, and of those roughly 7 million are undiagnosed. The global incidence of diabetes is predicted to grow to 552 million by 2030. Among people with diabetes, up to 4% annually will develop diabetic foot ulcers (DFU), and roughly 10 to 15 percent will have at least one foot ulcer during their lifetime. These diabetic ulcers are recurrent, painful, slow healing wounds that are prone to infection. In addition, 80% of all lower limb amputations in patients with diabetes are preceded by a DFU.

The standard treatment for DFU include initial sharp debridement, pressure relief, and infection control. However, despite these treatments, some wounds may take a long time to heal or not heal at all. The benefits of nitric oxide (NO) to wound healing are known. However, there are currently no practical therapies available which can deliver nitric oxide for wound healing in a controlled fashion directly to the wound.

Without wishing to be bound by theory, it is believed that the present compounds can effectively deliver NO to heal wounds such as those associated with DFU. For example, the present compounds may function as pro-drugs of NO with various advantages. For example, the compounds are shelf-stable and do not release NO until wound contact. In addition, the compounds do not require secondary activation other than application to the wound. The compounds can release large amounts of NO (e.g., each molecule of compound can decompose to release two molecules of NO). Further, the kinetics of release can be fine-tuned so as to adjust the dose of NO and the time over which that dose is released.

Figure 3:
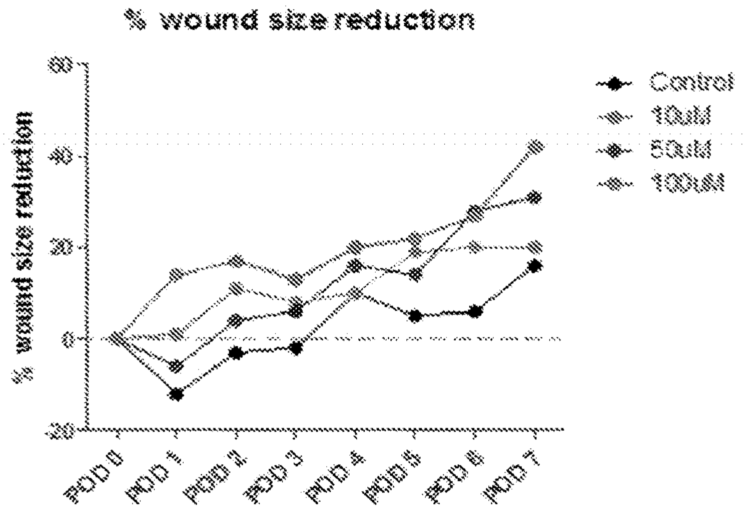
FIG. 3, panel A, shows dose-dependent effects on wound size by a compound of the invention formulated as hydrogels. Panel B shows effects on wound size area by a compound of the invention formulated in a hydrogel at 100 μM and 1000 μM. Panel C shows effects on vessel density by a compound of the invention. Panel D shows effects on the density of α-smooth muscle actin-positive myofibroblasts by a compound of the invention.
Figure 3:
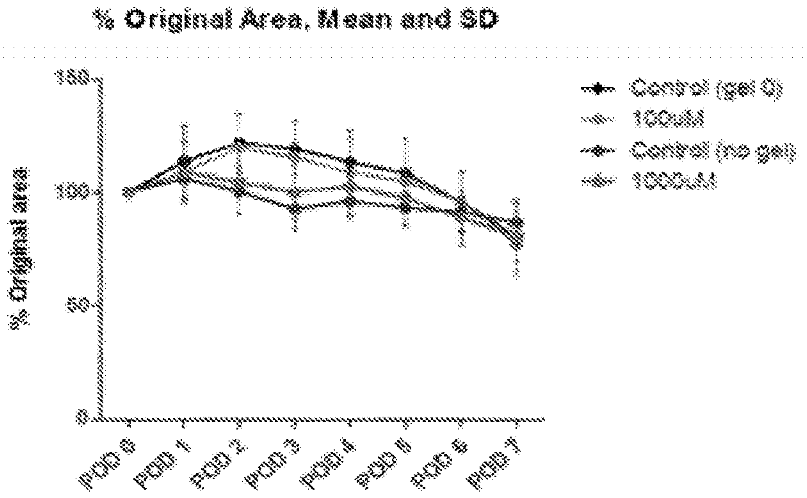
Figure 3:
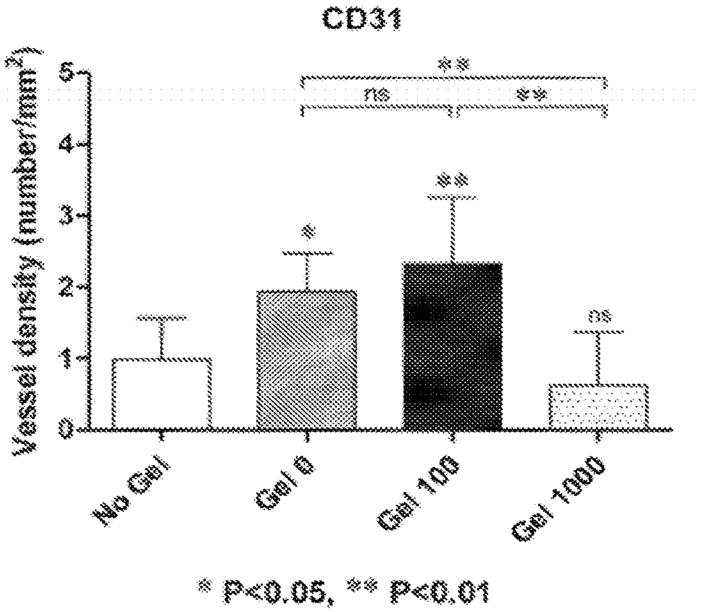
Figure 3:
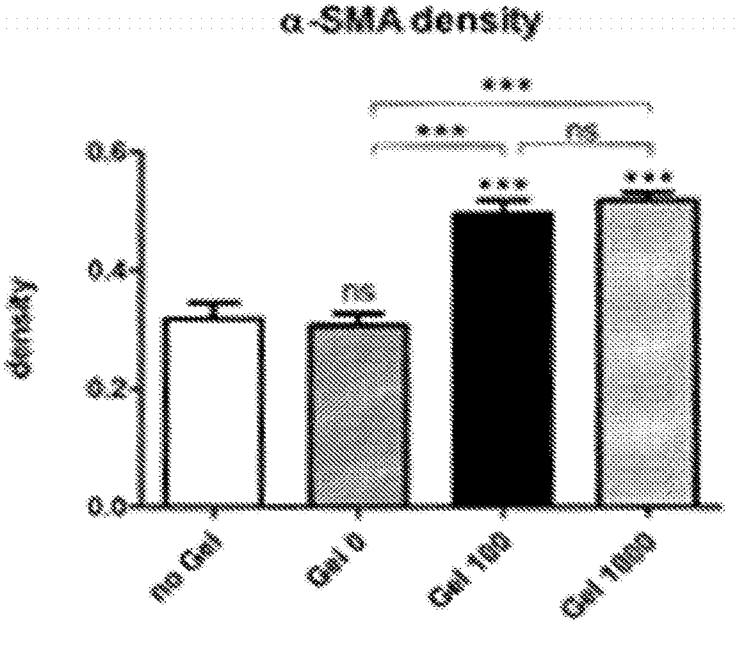

An initial dose range study was performed to study the effects of the compounds of the invention on wound healing. Five homozygous diabetic 8-12 weeks old, Lep/r-db/db male mice (strain C57BL/KsJ-Leprdb) were anesthetized with 60 mg/kg pentobarbital and disinfected with 70% alcohol. Subsequently, a 1-$cm^2$ full-thickness wound was excised on the dorsa of the mice. The mice were then treated with either PVA gel containing no test article (Control), PVA gel containing test article (i.e., compound 506-3-111) at 10 uM concentration, PVA gel containing test article at 50 uM concentration, or PVA gel containing test article at 100 uM concentration. Immediately after wounding, the experimental groups had the NO releasing gel material applied to the wound twice a day and the control group had only the un-medicated gel applied to the wound. Dressing changes were performed twice daily. On day 7, the animals were euthanized and the wound area with its surrounding skin and underlying tissue was excised en bloc. Tissues were fixed and retained. As shown in FIG. 3, panel A, there was a clear dose dependent reduction in wound size by the PVA gel containing test article versus PVA gel alone. Further, the compounds appeared to be well tolerated with no adverse effects or toxicity even at the highest dose. From this initial dose study, dose levels of 100 um and 1 mM were selected for additional studies.

Experiments were performed to study the effects of the gel formulation on wound healing in diabetic populations that often presents with non-healing wounds. Specifically, 48 homozygous diabetic 8-12 weeks old, Lep/r-db/db male mice (strain C57BL/KsJ-Leprdb) were anesthetized with 60 mg/kg pentobarbital and disinfected with 70% alcohol. Subsequently, a 1-$cm^2$ full-thickness wound was excised on the dorsa of the mice. The animals were then divided into 5 groups: 2 experimental groups (n=12 each, 24 in total) were treated with a gel product containing either 100 uM or 1 mM of NO releasing compounds, a control group (n=12) that was treated with the unmedicated gel (i.e. gel not containing NO releasing compound), and an untreated control group with wounds that remained untested (n=12). Immediately after wounding, the experimental groups had the NO releasing gel material applied to the wound twice a day while the control group had the un-medicated gel applied to the wound. Dressing changes were performed twice daily. On day 2, one cohort of the animals (n=30) was euthanized and fixed in 10% neutral-buffered formalin solution, with the treatment device in place to evaluate actual wound surface deformations. The wound area, surrounding skin, and underlying tissue were excised en bloc and kept in 70% alcohol at 4° C. until paraffin embedment was performed. On day 7, the remaining animals (n=30) were euthanized, and the wound area with its surrounding skin and underlying tissue were excised en bloc. Tissues were fixed in 10% neutral-buffered formalin solution for 24 hours and kept in 70% alcohol at 4° C. until paraffin embedment is performed. After fixing and appropriate staining, the tissue samples were analyzed for granulation tissue thickness on Day 7, density of α-smooth muscle actin-positive myofibroblasts, wound healing kinetics, blood vessel density, and cell proliferation on day 7, and tissue ingrowth.

Consistent with the previous study, the tested compounds in gel formulation appeared to be well tolerated with no adverse effects or toxicity at all concentrations. The effects of the compounds on vessel density is shown in FIG. 3, panel B.

Tissue samples were also submitted for histological examination. Specifically, four groups were submitted: no gel, gel without compound, gel with 100 uM compound, and gel with 1 mM compound. Each group had 3 slides. The slides were stained for IHC, CD 31, and α-SMA. The slides were scanned at 10× to generate about 14 images. Each slide had 6 views on which image analysis was performed (CD31: Image J-manual, α-SMA: Image pro-plus manual). Finally, statistical analysis was performed on the data obtained.

As shown in FIG. 3, panel C, the gel formulation with the test compounds had minimal effects on angiogenesis. However, there was a statistically significant increase in α-SMA associated with treatment with the test compounds suggesting a positive effect on remodeling of the wound bed (FIG. 3, panel D).

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

What is claimed is:

1. A composition comprising a compound and a carrier, wherein the compound is selected from:

(2)

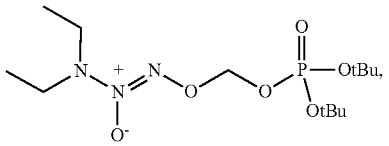

(14)

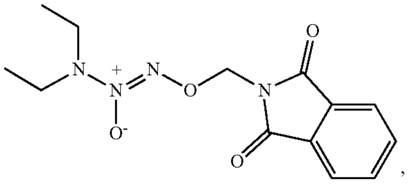

, (17)

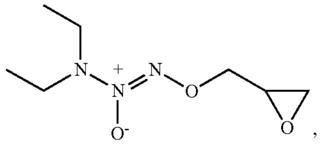

, (19)

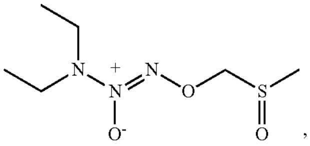

, (20)

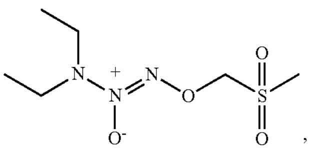

,

-continued (31)

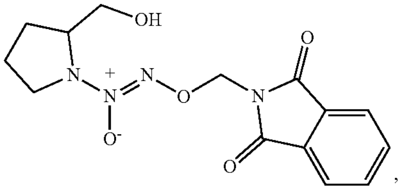

, (33)

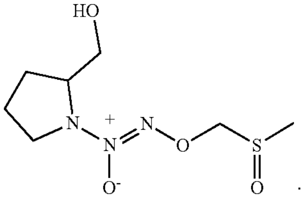

.

or a pharmaceutically acceptable salt, ester or prodrug thereof.

2. The composition of claim 1, wherein the compound is capable of releasing nitric oxide under physiological conditions.

3. A pharmaceutical composition, comprising the compound of claim 1 and a pharmaceutically acceptable carrier or excipient.

4. A method for treating a disorder of nitric oxide dysregulation comprising administering a therapeutically effective amount of the compound of claim 1 or a pharmaceutically acceptable salt, ester or prodrug thereof to a patient in need thereof.

5. The method of claim 4, wherein the disorder of nitric oxide dysregulation is one or more of a cardiovascular disorder, vasodilation, and erectile dysfunction.

6. The method of claim 4, wherein the disorder of nitric oxide dysregulation is a cardiovascular disorder.

7. The method of claim 4, wherein the disorder of nitric oxide dysregulation is a metabolic-related disorder.

8. The method of claim 4, wherein the disorder of nitric oxide dysregulation is a pulmonary disorder.

9. The method of claim 4, wherein the disorder of nitric oxide dysregulation is an intraocular pressure-associated disorder.

10. The method of claim 9, wherein the intraocular pressure-associated disorder is glaucoma.

11. The method of claim 4, wherein the disorder of nitric oxide dysregulation is ischemia.

12. The method of claim 4, wherein the disorder of nitric oxide dysregulation is infection.

13. The method of claim 4, wherein the disorder of nitric oxide dysregulation is cancer.

14. A method for enhancing or stimulating wound healing, comprising administering a therapeutically effective amount of the compound of claim 1 or a pharmaceutically acceptable salt, ester or prodrug thereof to a patient in need thereof.

15. A composition comprising a compound represented by one of the following compounds and a carrier:

(3)

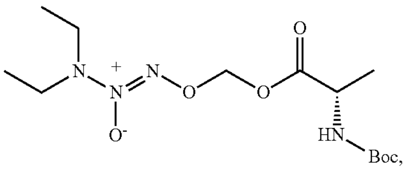

(4)

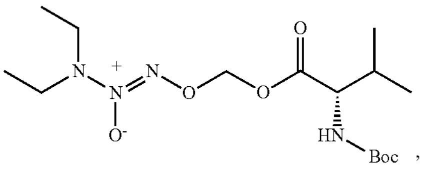

, (7)

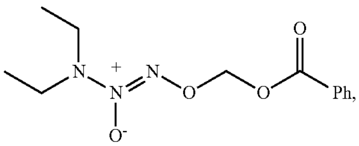

(8)

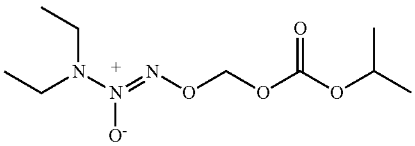

, (9)

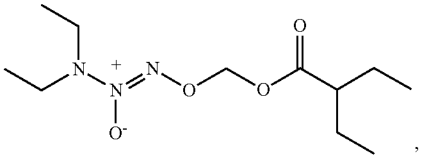

, (10)

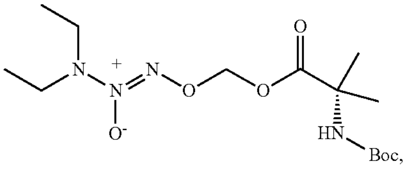

(11)

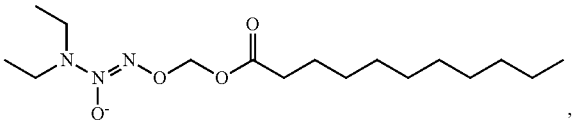

, (12)

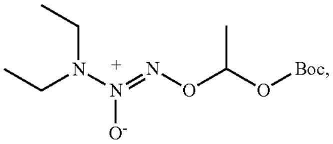

(13)

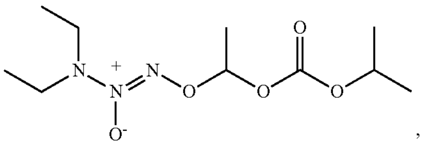

, (15)

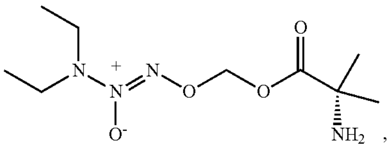

,

-continued
(16)
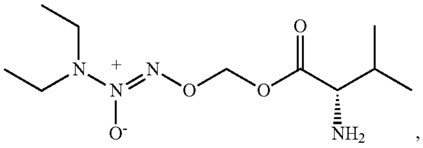
,
(21)
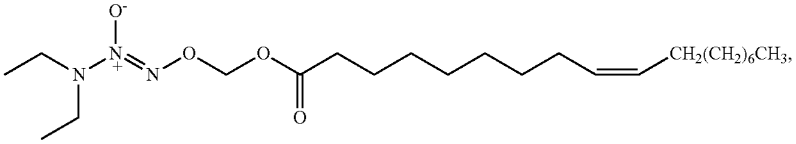
(22)
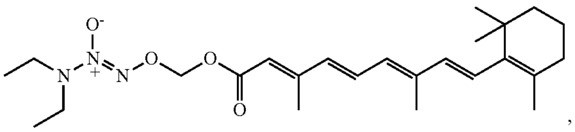
,
(23)
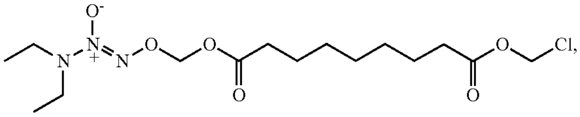
(24)
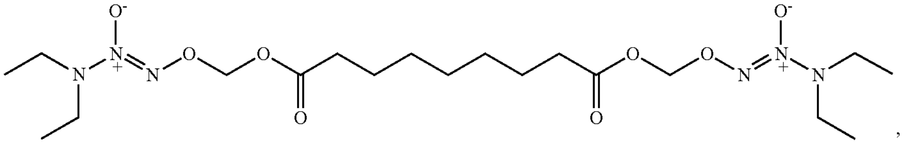
,
(26)
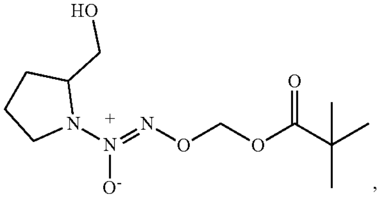
,
(27)
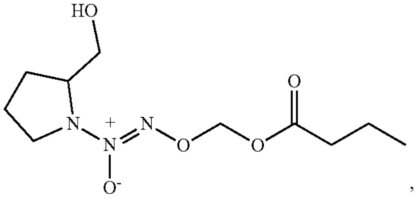
, and
(30)
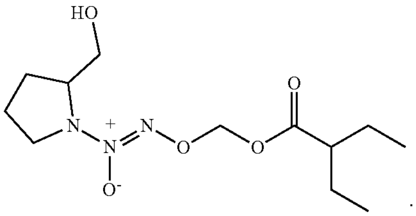
.
16. The composition of claim 15, wherein the compound is capable of releasing nitric oxide under physiological conditions.
17. The composition of claim 15 further comprising a pharmaceutically acceptable carrier or excipient.
18. The method of claim 4, wherein the disorder of nitric oxide dysregulation is bacterial infection.
* * * * *